United States Patent [19]
Johnson et al.

[11] Patent Number: 5,947,921
[45] Date of Patent: Sep. 7, 1999

[54] CHEMICAL AND PHYSICAL ENHANCERS AND ULTRASOUND FOR TRANSDERMAL DRUG DELIVERY

[75] Inventors: Mark E. Johnson, Allston; Samir S. Mitragotri, Cambridge; Daniel Blankschtein, Brookline; Robert S. Langer, Newton; Michael Pishko, Arlington, all of Mass.; Joseph Kost, Omer, Israel

[73] Assignee: Massachusetts Institute of Technology, Cambridge, Mass.

[21] Appl. No.: 08/574,377

[22] Filed: Dec. 18, 1995

[51] Int. Cl.⁶ .................................................. A61B 17/00
[52] U.S. Cl. .................................................. 604/22; 601/2
[58] Field of Search .................. 604/20, 22, 49; 128/760, 637; 601/2

[56] References Cited

U.S. PATENT DOCUMENTS

| | | |
|---|---|---|
| 3,551,554 | 12/1970 | Herschler . |
| 3,711,602 | 1/1973 | Herschler . |
| 3,711,606 | 1/1973 | Herschler . |
| 4,002,221 | 1/1977 | Buchalter . |
| 4,127,125 | 11/1978 | Takemoto et al. . |
| 4,144,646 | 3/1979 | Takemoto et al. . |
| 4,176,664 | 12/1979 | Kalish . |
| 4,249,531 | 2/1981 | Hiller et al. . |
| 4,280,494 | 7/1981 | Cosgrove, Jr. et al. . |
| 4,309,989 | 1/1982 | Fahim . |
| 4,372,296 | 2/1983 | Fahim . |
| 4,537,776 | 8/1985 | Cooper .................................. 514/424 |
| 4,557,943 | 12/1985 | Rosler et al. . |
| 4,563,184 | 1/1986 | Korol . |
| 4,646,725 | 3/1987 | Moasset . |
| 4,698,058 | 10/1987 | Greenfeld et al. . |

(List continued on next page.)

FOREIGN PATENT DOCUMENTS

| | | |
|---|---|---|
| 0 043738 B1 | 10/1985 | European Pat. Off. ......... A61K 9/06 |
| 386408 A2 | 5/1990 | European Pat. Off. . |
| 612525 A1 | 8/1994 | European Pat. Off. . |
| 27 56 460A1 | 6/1979 | Germany ....................... A61M 37/00 |
| 3-170172 | 7/1991 | Japan ............................... A61N 1/30 |
| 445433 | 11/1974 | U.S.S.R. ......................... A61H 23/00 |
| 556805 | 6/1977 | U.S.S.R. ......................... A61H 23/00 |
| 591186 | 1/1978 | U.S.S.R. ............................. A61F 9/00 |
| 0910157 | 2/1978 | U.S.S.R. ......................... A61H 23/00 |
| 506421 | 2/1978 | U.S.S.R. ......................... A61M 37/00 |
| 1 577 551 | 2/1976 | United Kingdom ........... A61K 33/30 |
| 2153223 | 8/1985 | United Kingdom ........... A61K 47/00 |
| WO 88/00001 | 1/1988 | WIPO . |
| WO 90/01971 | 3/1990 | WIPO . |
| WO 91/12772 | 9/1991 | WIPO ............................. A61B 17/00 |
| WO 93/20745 | 10/1993 | WIPO ............................... A61B 5/00 |

OTHER PUBLICATIONS

Egorov, E.A. et al., "Use of the Variants of the Pharmacophysical Influence in Ophthalmology", 102 Ophthalmology Journal #2 (1992).

Eppstein, D.A. et al., "Applications of Liposome Formulations for Antimicrobial/Antiviral Therapy" Liposomes as Drug Carriers 311, 315 (G. Gregoriadis ed. 1988).

(List continued on next page.)

*Primary Examiner*—Mark Bockelman
*Attorney, Agent, or Firm*—Arnall Golden & Gregory, LLP

[57] ABSTRACT

Transdermal transport of molecules during sonophoresis (delivery or extraction) can be further enhanced by providing chemical enhancers which increase the solubility of the compound to be transported and/or lipid bilayer solubility, and/or additional driving forces for transport, such as mechanical or osmotic pressure, magnetic fields, electroporation or iontophoresis. In a preferred embodiment the ultrasound is low frequency ultrasound which induces cavitation of the lipid layers of the stratum corneum (SC). This method provides higher drug transdermal fluxes, allows rapid control of transdermal fluxes, and allows drug delivery or analyte extraction at lower ultrasound intensities and other forces or concentrations than that required if each means of enhancing transport is used individually.

13 Claims, 5 Drawing Sheets

U.S. PATENT DOCUMENTS

| | | |
|---|---|---|
| 4,767,402 | 8/1988 | Kost et al. .............................. 604/22 |
| 4,780,212 | 10/1988 | Kost et al. . |
| 4,820,720 | 4/1989 | Sanders et al. ......................... 514/356 |
| 4,821,740 | 4/1989 | Tachibana et al. . |
| 4,834,978 | 5/1989 | Nuwayser . |
| 4,855,298 | 8/1989 | Yamada et al. . |
| 4,860,058 | 8/1989 | Kobayashi et al. . |
| 4,863,970 | 9/1989 | Patel et al. ............................. 514/784 |
| 4,953,565 | 9/1990 | Tachibana et al. . |
| 5,006,342 | 4/1991 | Cleary et al. . |
| 5,007,438 | 4/1991 | Tachibana et al. . |
| 5,016,615 | 5/1991 | Driller . |
| 5,019,034 | 5/1991 | Weaver et al. ........................... 604/20 |
| 5,076,273 | 12/1991 | Schoendorfer et al. . |
| 5,115,805 | 5/1992 | Bommannan et al. .................... 604/20 |
| 5,139,023 | 8/1992 | Stanley et al. . |
| 5,140,985 | 8/1992 | Schroder et al. . |
| 5,171,215 | 12/1992 | Flanagan ................................. 604/22 |
| 5,197,946 | 3/1993 | Tachibana . |
| 5,231,975 | 8/1993 | Bommannan et al. .................... 604/20 |
| 5,267,985 | 12/1993 | Shimada et al. .......................... 604/22 |
| 5,315,998 | 5/1994 | Tachibana et al. ................ 128/660.01 |
| 5,323,769 | 6/1994 | Bommannan et al. ..................... 601/2 |
| 5,386,837 | 2/1995 | Sterzer . |
| 5,401,237 | 3/1995 | Tachibana et al. . |
| 5,405,614 | 4/1995 | D'Angelo et al. . |
| 5,415,629 | 5/1995 | Henley . |
| 5,421,816 | 6/1995 | Lipkovker ................................ 604/20 |
| 5,445,611 | 8/1995 | Eppstein et al. ......................... 604/49 |
| 5,458,140 | 10/1995 | Eppstein et al. ........................ 128/760 |
| 5,582,586 | 12/1996 | Tachibana et al. ....................... 604/22 |
| 5,658,247 | 8/1997 | Henley .................................... 604/20 |

OTHER PUBLICATIONS

Eppstein, D.A., "Medical Utility of Interferons: Approaches to Increasing Therapeutic Efficacy" 7 Pharmacy International 195–198 (1986).

Eppstein, D.A. et al., "Alternative Delivery Systems for Peptides and Proteins as Drugs" 5 CRC Reviews in Therapeutic Drug Carrier Systems 99, 125 (1988).

Loshilov, V.I. et al., "Research of the Technological Process of Ultrasound Treatment of Infected Wounds" (1976).

Ulashik, V.S. et al., Ultrasound Therapy (Minsk, Belarus 1983).

Apfel, R.F., "Possiblity of Microcavitation from Diagnostic Ultrasound," *IEEE Trans. Ultrason. Ferroelectrics Freq. Control* UFFC–33:139–142 (1986).

Aungst, et al., "Contributions of Drug Solubilization, Partitioning, Barrier Disruption, and Solvent Permeation to the Enhancement of Skin Permeation of Various Compounds with Fatty Acids and Amines," *Pharm. Res.* 7:712–718 (1990).

Barry, "Mode of Action of Penetration Enhancers in Human Skin," *J. Controlled Rel.* 6:85–97 (1987).

Bommer, et al., "Subcutaneous Erythropoeitin," *Lancet* 406 (1988).

Burnette, R. R., "Iontophoresis," *Transdermal Drug Delivery Developmental Issues and Research Initiatives* (Hadgraft and Guv. Editors, Marcel Dekker, 247–291, 1989).

Cleary, Gary W., "Transdermal Controlled Release Systems," Medical Applications of Controlled Release (Langer and Wise, Editors, CRC Press 203–251, 1984).

Clegg and Vaz, "Translational diffusion of proteins and lipids in artificial lipid bilayer membranes. A comparison of experiment with theory," *Progress in Protein–Lipid Interactions* Watts, ed. (Elsvier, NY 1985) Chapter 5:173–229.

Davis, J.,et al., "Characterization of Recombinant Human Erythropoietin Produced in Chinese Hamster Ovary Cells," *Biochemistry* 26:2633–2638 (1987).

Ebert, et al., "Transbuccal Absorption of Diclofenac Sodium in a Dog Model," *Controlled Release Technology Pharmaceutial Application* (Lee, et al. Editors, American Chemical Society)310–321 (1987).

Eggerth, et al., "Evaluation of Hamster Cheek Pouch as a Model for Buccal Absorption," *Proceed. Intern. Symp. Rel. Bioact. Mater.,*(Controlled Release Society, Inc.) 14:180–181 (1987).

D'Emanuele, et al., "An Investigation of the Effects of Ultrasound on Degradable Polyanhydride Matrices," *Macromolecules* 25:511–515 (1992).

Elias, "The Microscopic Structure of the Epidermis and Its Derivatives," *Percutaneous Absorption: Mechanisms–Methodology–Drag Delivery* (Bronaugh, R. L., Maibach, H., Editors, Marcel Dekker, New York,) 1–12 (1989).

Flynn, G. L., "Mechanism of Percutaneous Absorption from Physiochemical Evidence," *Percutaneous Absorption: Mechanisms–Methodology–Drug Delivery* (Bronaugh, R.L., Maibach, H., Editors, Marcel Dekker, New York) 27–51 (1989).

Friedman, R. M., 'Interferons: A Primer', (Academic Press, New York, 1981).

Gaertner, W., "Frequency Dependence of Ultrasonice Cavitation," *J. Acoust. Soc. Am.* 26:977–980 (1954).

Ghanem et al., "The effects of ethanol on the transport of lipophilic and polar permeants across hairless mouse skin: Methods/validation of a novel approach," *Int. J. Pharm.* 78:137–156 (1992).

Grups and Frohmuller, "Cyclic Interferon Gamma Treatment of Patients with Metastatic Renal Carcinoma," *J. Med.* 64(3):218–220 (1989).

Hansch and Leo, "Substitutent Constants for Correlation Analysis in Chemistry and Biology" (1979).

Junginger, et al., "Visualization of Drug Transport Across Human Skin and the Influence of Penetration Enhancers," *"Drug Permeation Enhancement"* (Hsieh, D.S., Editors, Marcel Dekker, Inc. New York) 59–89 (1994).

Kasting, et al., "Prodrugs for Dermal Delivery: Solubility, Molecular Size, and Functional Group Effects," "Prodrugs: Topical and Ocular Delivery" Sloan, ed. (Marcel Dekker, NY 1992) 117–161.

Kost and Langer, "Ultrasound–Mediated Transdermal Drug Delivery," *Topical Drug Bioavailability Bioequivalence and Penetration* (Maibach, H. I., Shah, V. P., Editors, Plenum Press, New York) 91–104 (1993).

Kost, et al., "Ultrasound Effect on Transdermal Drug Delivery," (Ben Gurion University Dept. of Chem. Engineering, Beer Sheva Israel) (MIT, Dept. of Applied Biological Sciences, Cambridge, MA) CRS Aug. 1986.

Krall, L.P., 'World Book of Diabetes in Practice' (Editors, Elsvier, 1988).

Lee, V. H. L., et al., "Protease Inhibition as an Additional Mechanism for the Nasal Absorption Enhancement Effect of Sodim Taurodihydrofusidate," *Proceed. Intern. Symp. Control. Rel. Bioact. Mater* 14:55–56 (1987).

Lee, V. H. L., et al., "Nasal Peptide and Protein Absorption Promotors: Aminopeptidase Inhibition as a Predictor of Absorption Enhancement Potency of Bile Salts," *Proceed. Intern. Symp. Control. Rel. Bioact. Mater* 14:53–54 (1987).

Levy, et al., "Effect of Ultrasound on Transdermal Drug Delivery to Rats and Guinea Pigs," *J. Clin. Invest.* 83:2074–2078 (1989).

Liu, et al., "Contransport of Estradiol and Ethanol Through Human Skin In Vitro: Understanding the Permeant/Enhancer Flux Relationship," *Pharmaceutical Research* 8:938–944 (1991).

Liu, et al., "Experimental Approach To Elucidate the Mechanism of Ultrasound–Enhanced Polymer Erosion and Release of Incorporated Substances," *Macromolecules* 25:123–128 (1992).

Machluf and Kost, "Ultrasonically enhanced transdermal drug delivery. Experimental approaches to elucidate the mechanism," *J. Biomater. Sci. Polymer Edn.* 5:147–156 (1993).

Mak, et al., "Oleic Acid Concentration and Effect in Human Stratum Corneum: Non–Invasive Determination by Attenuated Total Reflectance Infared Spectroscopy In Vivo," *J. Controlled Rel.* 12:67–75 (1990).

Mitragotri, et al., "Ultrasound–Mediated Transdermal Protein Delivery," *Science* 269:850–853 (1995).

Mitragotri, et al., "A Mechanistic Study of Ultrasonically–Enhanced Transdermal Drug Delivery," *J. Pharm. Sci.* 84:697–706 (1995).

Morimoto, Y., et al., "Prediction of Skin Permeability of Drugs: Comparison of Human and Hairless Rat Skin," *J. Pharm. Pharmacol.* 44:634–639 (1991).

Nagai and Konishi, "Buccaal/Gingival Drug Delivery Systems," *Journal of Controlled Release* (Elsevier Science Publishers B.V., Amsterdam) 6:353–360 (1987).

Newman, J., et al., "Hydrocortisone Phonophoresis," *J. Am. Pod. Med. Assoc.* 82:432–435 (1992).

Olanoff and Gibson, "Method to Enhance Intranasal Peptide Delivery," *Controlled Release Technology Pharmaceutical Application* (Lee, et al. Editors, American Chemical Society) 301–309 (1987).

Ongpipattanankul, et al., "Evidence that Oleic Acid Exists in a Separate Phase Within Stratum Corneum Lipids," *Pharm. Res.* 8:350–354 (1991).

Parkin, et al., "Atopic manifestations in the acquired immune deficiency syndrome: response to recombinant interferon gamma," *Br. Med. J.,* 294:1185–1186 (1987).

Perry, et al., "Perry's Chemical Engineering Handbook" (McGraw–Hill, NY 1984).

Pishko, et al., "Amperometric Glucose Microelectrodes Prepared through Immobilization of Glucose Oxidase in Redox Hydrogels," *Anal. Chem.* 63:2268–2272 (1991).

Potts and Guy, "Predicting Skin Permeability," *Pharm. Res.* 9:663–669 (1992).

Prausnitz, et al., "Electroporation of mammalian skin:A mechanism to enhance transdermal drug delivery," *Proc. Natl. Acad. Sci. USA* 90:10504–10508 (1993).

Quillen, W.S., "Phonophoresis: A Review of the Literature and Technique," *Athl. Train.* 15:109–110 (1980).

Robinson & Lee, "Influence of Drug Properties on Design," *Controlled Drug Delivery* 42–43.

Rosell, J., et al., "Skin Impedance From 1 Hz to 1 MHz," *IEEE Trans. Biomed. Eng.* 35:649–651 (1988).

Skauen, et al., "Phonophoresis," *Int. J. Pharm.* 20:235–245 (1984).

Stringfellow, *Clinical Applications of interferons and their inducers,* (Editors, Marcel Dekker, New York, 1986).

Tamada, et al., *Proceed. Intern. Symp. Control. Rel. Bioact. Mater.* 22, 129–130 (1995).

Tocanne, et al., "Lipid lateral diffusion and membrane organization," *FEB* 257:10–16 (1989).

Tyle and Agrawala, "Drug Delivery by Phonophoresis," *Pharm. Res.* 6:355–361 (1989).

Walker and Hadgraft, "Oleic acid—a membrane 'fluidiser' or fluid within the membrane," *Int. J. Pharm.* 71:R1–R4 (1991).

Walmsley, "Applications of Ultrasound in Dentistry," *Ultrasound in Med. and Biol.* 14:7–14 (1988).

Walters, K. A., "Penetration Enhancers and Their Use in Transdermal Therapeutic Systems," *Transdermal Drug Delivery: Developmental Issues and Research Initiatives,* 197–246 (Hadgraft J., Guy, R.H., Editors, Marcel Dekker, 1989).

Wester and Mailbach, "Animal Models for Percutaneous Absorption," *Topical Drug Bioavailability Bioequivalence and Penetration* (Shah and Maibach, Editors, Plenum Press, New York) 333–349, (1993).

Wheatley, et al., "Use of Ussing Chamber for Investigation of Drug Delivery Across Viable Nasal Tissue Membranes," *Proceed. Intern. Symp. Control. Rel. Bioact. Mater.* (Controlled Release Society, Inc. 14:26–27 (1987).

Williams, et al., "On the non–Gaussian distribution of human skin permeabilities," *Int. J. Pharm.* 86:69–77 (1992).

Wilschut, et al., "Estimating Skin Permeation, The Validation of Five Mathematical Skin Permeation Models," *Chemosphere* 30:1275–1296 (1995).

CHEMICAL AND PHYSICAL ENHANCERS AND ULTRASOUND FOR TRANSDERMAL DRUG DELIVERY

BACKGROUND OF THE INVENTION

The present invention generally relates to improved methods for drug delivery and measurement of analyte using ultrasound in combination with chemical and/or physical enhancers of transport.

The United States government has rights in this invention by virtue of NIH grant GM44884 to R. Langer.

Transdermal drug delivery (TDD) offers several advantages over traditional delivery methods including injections and oral delivery. When compared to oral delivery, TDD avoids gastrointestinal drug metabolism, reduces first-pass effects, and provides sustained release of drugs for up to seven days, as reported by Elias, In *Percutaneous Absorption: Mechanisms— Methodoloqy-Drag Delivery*, Pronaugh, R. L., Maibach, H. 1. (Ed), pp 1–12, Marcel Dekker, New York, 1989. The word "transdermal" is used herein as a generic term. However, in actuality, transport of drugs occurs only across the epidermis where the drug is absorbed in the blood capillaries. When compared to injections, TDD eliminates the associated pain and the possibility of infection. Theoretically, the transdermal route of drug administration could be advantageous in the delivery of many therapeutic proteins, because proteins are susceptible to gastrointestinal degradation and exhibit poor gastrointestinal uptake, proteins such as interferons are cleared rapidly from the blood and need to be delivered at a sustained rate in order to maintain their blood concentration at a high value, and transdermal devices are easier to use than injections.

In spite of these advantages, very few drugs and no proteins or peptides are currently administered transdermally for clinical applications because of the low skin permeability to drugs. This low permeability is attributed to the stratum corneum (SC), the outermost skin layer which consists of flat, dead cells filled with keratin fibers (keratinocytes) surrounded by lipid bilayers. The highly-ordered structure of the lipid bilayers confers an impermeable character to the SC (Flynn, G. L., In *Percutaneous Absorption: Mechanisms-Methodology-Drug Delivery.;* Bronaugh, R. L., Maibach, H. I. (Ed), pages 27–53, Marcel Dekker, New York, 1989).

A variety of approaches have been suggested to enhance transdermal transport of drugs. These include: i) use of chemicals to either modify the skin structure or to increase the drug concentration in the transdermal patch (Junginger, et al. In *"Drug Permeation Enhancement"*; Hsieh, D. S., Eds., pp. 59–90 (Marcel Dekker, Inc. New York 1994; Burnette, R. R. In *Developmental Issues and Research Initiatives;* Hadgraft J., G., R. H., Eds., Marcel Dekker: 1989; pp. 247–288); ii) applications of electric fields to create transient transport pathways [electroporation] (Prausnitz *Proc. Natl. Acad. Sci.USA* 90, 10504–10508 (1993); Walters, K. A., in *Transdermal Drug Delivery: Developmental Issues and Research Initiatives,* Ed. Hadgraft J., Guy, R. H., Marcel Dekker, 1989) or to increase the mobility of charged drugs through the skin [iontophoresis], and iii) application of ultrasound [sonophoresis].

Electroporation is believed to work in part by creating transient pores in the lipid bilayers of the SC (Burnett (1989)). Iontophoresis provides an electrical driving force to move compounds.

Chemical enhancers have been found to increase transdermal drug transport via several different mechanisms, including increased solubility of the drug in the donor formulation, increased partitioning into the SC, fluidization of the lipid bilayers, and disruption of the intracellular proteins (Kost and Langer, In Topical Drug Bioavailability, Bioequivalence, and Penetration; Shah and Maibech, ed. (Plennum, N.Y. 1993) pp. 91–103 (1993)).

Ultrasound has been shown to enhance transdermal transport of low-molecular weight drugs (molecular weight less than 500) across human skin, a phenomenon referred to as sonophoresis (Levy, *J. Clin Invest.* 1989, 83, 2974–2078; Langer, R., In *"Topical Drug Bioavailability, Bioequivalence, and Penetration"*; pp. 91–103, Shah V. P., M.H.I., Eds. (Plenum: New York, 1993); Frideman, R. M., *'Interferons: A Primer'*, Academic Press, New York, 1981)). Ultrasound has been shown to create cavitation within the SC, which disorders the lipid bilayers and increases drug transport (Walters, In Transdermal Drug Delivery: Developmental Issues and Research Initiatives, Hadraft, ed. (Marcel Dekker, 1989) pp. 197–233).

U.S. Pat. Nos. 4,309,989 to Fahim and 4,767,402 to Kost, et al., disclose various ways in which ultrasound has been used to achieve transdermal drug delivery. Sonophoresis has been shown to enhance transdermal transport of various drugs. Although a variety of ultrasound conditions have been used for sonophoresis, the most commonly used conditions correspond to the therapeutic ultrasound (frequency in the range of 1 MHz–3 MHz, and intensity in the range of 0–2 W/cm$^2$) (Kost, *In Topical Drug Bioavailability Bioequivalence and Penetration,* pp. 91–103, Maibach, H. I., Shah, V. P. (Ed) Plenum Press, New York, 1993; U.S. Pat. No. 4,767,402 to Kost, et al.).

U.S. Pat. No. 5,445,611 to Eppstein, et al., describes enhancement of ultrasound using the combination of chemical enhancers with modulation of the frequency, intensity, and/or phase of the ultrasound to induce a type of pumping action. However, the intensity and frequencies used in the examples are quite high, which generates heat and decreasing transport over time.

In a recent study of sonophoresis, it has been shown that application of ultrasound at therapeutic frequencies (1 MHz) induces growth and oscillations of air pockets present in the keratinocytes of the SC (a phenomenon known as cavitation). These oscillations disorganize the SC lipid bilayers thereby enhancing transdermal transport.

However, application of therapeutic ultrasound does not induce transdermal transport of high-molecular weight proteins. It is a common observation that the typical enhancement induced by therapeutic ultrasound is less than ten-fold. In many cases, no enhancement of transdermal drug transport has been observed upon ultrasound application. Accordingly, a better selection of ultrasound parameters is needed to induce a higher enhancement of transdermal drug transport by sonophoresis. Moreover, although efficacy to some degree has been observed using ultrasound for transport of other compounds, the efficiency of transport under conditions acceptable to patients has not been achieved.

It is therefore an object of the present invention to provide a method and means for enhancing transdermal transport.

It is a further object of the present invention to provide methods for using ultrasound in combination with other means of enhancement for drug delivery and collection of analyte in an efficient, practical manner.

SUMMARY OF THE INVENTION

Transdermal transport of molecules during sonophoresis (delivery or extraction) can be further enhanced by providing chemical enhancers which increase the solubility of the compound to be transported and/or lipid bilayer solubility, or additional driving forces for transport, such as, mechanical force fields, magnetic fields or iontophoresis. In a preferred embodiment, the ultrasound is low frequency ultrasound which induces cavitation of the lipid layers of the stratum corneum (SC). This method i) provides higher transdermal fluxes, ii) allows rapid control of transdermal fluxes, and iii) allows drug delivery or analyte extraction at lower ultrasound intensities and other forces or concentrations than that required if each means of enhancing transport is used individually.

DETAILED DESCRIPTION OF THE INVENTION

Figure 1:
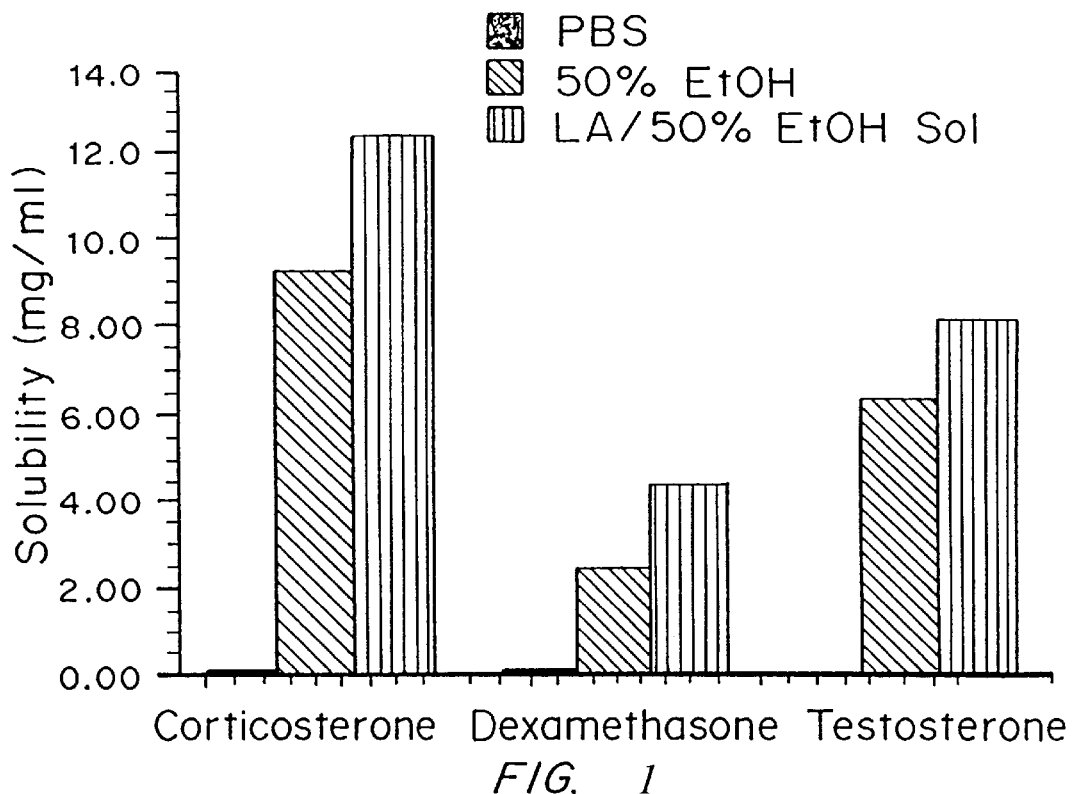
FIG. 1 is a graph of solubility (mg/ml) for corticosterone, dexamethasone, and testosterone in PBS (dark bar), 50% ethanol (hatched \\\\) and linoleic acid in 50% ethanol (striped ||||).

Sonophoresis:

As used herein, sonophoresis is the application of ultrasound to the skin, alone or in combination with chemical enhancers, iontophoresis, electroporation, magnetic force fields, mechanical pressure fields or electrical fields, to facilitate transport of a compound through the skin. In one embodiment, a drug, alone or in combination with a carrier, penetration enhancer, lubricant, or other pharmaceutically acceptable agent for application to the skin, is applied to the skin. In another embodiment, the compound is an analyte such as glucose which is present in a body fluid and extracted by application of the ultrasound, alone or in combination with other forces and/or chemical enhancers.

Ultrasound is defined as sound at a frequency of between 20 kHz and 10 MHz, with intensities of between greater than 0 and 3 W/cm$^2$. Ultrasound B preferably administered at frequencies of less than or equal to about 2.5 MHz to induce cavitation of the skin to enhance transport. As used herein, "low frequency" sonophoresis is ultrasound at a frequency that is less than 1 MHz, more typically in the range of 20 to 40 KHz, which can be applied continuously or in pulses, for example, 100 msec pulses every second, at intensities in the range of between zero and 1 W/cm$^2$, more typically between 12.5 mW/cm$^2$ and 225 mW/cm$^2$. Exposures are typically for between 1 and 10 minutes, but may be shorter and/or pulsed. It should be understood that although the normal range of ultrasound is 20 kHz, one could achieve comparable results by varying the frequency to slightly more or less than 20 kHz. The intensity should not be so high as to raise the skin temperature more than about one to two degrees Centigrade.

Application of low-frequency (20 kHz) ultrasound dramatically enhances transdermal transport of drugs. Transdermal transport enhancement induced by low-frequency ultrasound was found to be as much as 1000-fold higher than that induced by therapeutic ultrasound (frequency in the range of 1 MHz–3 MHz, and intensity in the range of 0–2 W/cm$^2$). Another advantage of low-frequency sonophoresis as compared to therapeutic ultrasound is that the former can induce transdermal transport of drugs which do not passively permeate across the skin. Application of low-frequency ultrasound appears to induce cavitation inside as well as outside the skin. Cavitation occurring at either location may cause disordering of the SC lipids. In addition, oscillations of cavitation bubbles may result in significant water penetration into the disordered lipid regions. This may cause the formation of aqueous channels through the intercellular lipids of the SC. This allows permeants to transport across the disordered lipid domains, then across keratinocytes and the entire SC. This transport pathway may result in an enhanced transdermal transport as compared to passive transport because the diffusion coefficients of permeants through water, which is likely to primarily occupy the channels generated by ultrasound, are up to 1000-fold higher than those through the ordered lipid bilayers, and the transport path length of these aqueous channels may be much shorter (by a factor of up to 25) than that through the tortuous intercellular lipids in the case of passive transport.

Many ultrasound devices are available commercially which can be used in the method described herein. For example, the ultrasonic devices used by dentists to clean teeth have a frequency of between about 25 and 40 KHz. Commercially available portable ultrasound tooth-brushes make use of a small sonicator contained within the toothbrush (Sonex International Corporation). This sonicator is portable and operates on rechargeable batteries. Small pocket-size sonicators carried by patients and used to "inject" drugs whenever required could be readily adapted from these devices. In addition, these devices could be combined with sensors that can monitor drug concentrations in the blood to formulate a self-controlled drug (insulin, for example) delivery method that can decrease the attention required by the patient.

Devices typically used for therapeutic or diagnostic ultrasound operate at a frequency of between 1.6 and 10 MHz. These devices can also be modified for use at lower frequencies.

Lipid Bilayer Disrupting Agents

Chemical enhancers have been found to increase drug transport by different mechanisms. In the preferred embodiment described herein, chemicals which enhance the solubility of compounds to be delivered or measured are used in combination with chemicals which enhance permeability through lipids. Many chemicals having these properties are known and commercially available. For example, ethanol has been found to increase the solubility of drugs up to 10,000-fold (Mitragotri, et al. In *Encl. of Pharm. Tech.*: Swarbrick and Boylan, eds. Marcel Dekker 1995) and yield a 140-fold flux increase of estradiol, while unsaturated fatty acids have been shown to increase the fluidity of lipid bilayers (Bronaugh and Maiback, editors (Marcel Dekker 1989) pp. 1–12).

Examples of fatty acids which disrupt lipid bilayer include linoleic acid, capric acid, lauric acid, and neodecanoic acid, which can be in a solvent such as ethanol or propylene glycol. Evaluation of published permeation data utilizing lipid bilayer disrupting agents agrees very well with the observation of a size dependence of permeation enhancement for lipophilic compound, as discussed below. The permeation enhancement of three bilayer disrupting compounds, capric acid, lauric acid, and neodecanoic acid, in propylene glycol has been reported by Aungst, et al. *Pharm. Res.* 7, 712–718 (1990). They examined the permeability of four lipophilic compounds, benzoic acid (122 Da), testosterone (288 Da), naloxone (328 Da), and indomethacin (359 Da) through human skin. The permeability enhancement of each enhancer for each drug was calculated according to $\epsilon_{c/pg}=P_{e/pg}/P_{pg}$, where $P_{e/pg}$ is the drug permeability from the enhancer/propylene glycol formulation and $P_{pg}$ is the permeability from propylene glycol alone.

The primary mechanism by which unsaturated fatty acids, such as linoleic acid, are thought to enhance skin permeabilities is by disordering the intercellular lipid domain. For example, detailed structural studies of unsaturated fatty acids, such as oleic acid, have been performed utilizing differential scanning calorimetry Barry *J. Controlled Release* 6, 85–97 (1987) and infrared spectroscopy ongpipattanankul, et al., *Pharm. Res.* 8, 350–354 (1991); Mark, et al., *J. Control. Rel.* 12, 67–75 (1990). Oleic acid was found to disorder the highly ordered SC lipid bilayers, and to possibly form a separate, oil-like phase in the intercellular domain. SC lipid bilayers disordered by unsaturated fatty acids or other bilayer disrupters may be similar in nature to fluid phase lipid bilayers.

A separated oil phase should have properties similar to a bulk oil phase. Much is known about transport in fluid bilayers and bulk oil phases. Specifically, diffusion coefficients in fluid phase, for example, dimyristoylphosphatidylcholine (DMPC) bilayers Clegg and Vaz In "Progress in Protein-Lipid Interactions" Watts, ed. (Elsvier, N.Y. 1985) 173–229; Tocanne, et al., *FEB* 257, 10–16 (1989) and in bulk oil phase Perry, et al., "Perry's Chemical Engineering Handbook" (McGraw-Hill, NY 1984) are greater than those in the SC, and more importantly, they exhibit size dependencies which are considerably weaker than that of SC transport Kasting, et al., In: "Prodrugs: Topical and Ocular Delivery" Sloan, ed. (Marcel Dekker, NY 1992) 117–161; Potts and Guy, Pharm. Res. 9, 663–339 (1992); Willschut, et al., *Chemosphere* 30, 1275–1296 (1995). As a result, the diffusion coefficient of a given solute will be greater in a fluid bilayer, such as DMPC, or a bulk oil phase than in the SC. Due to the strong size dependence of SC transport, diffusion in SC lipids is considerably slower for larger compounds, while transport in fluid DMPC bilayers and bulk oil phases is only moderately lower for larger compounds. The difference between the diffusion coefficient in the SC and those in fluid DMPC bilayers or bulk oil phases will be greater for larger solutes, and less for smaller compounds. Therefore, the enhancement ability of a bilayer disordering compound which can transform the SC lipids bilayers into a fluid bilayer phase or add a separate bulk oil phase should exhibit a size dependence, with smaller permeability enhancements for small compounds and larger enhancements for larger compounds.

A comprehensive list of lipid bilayer disrupting agents is described in European Patent Application 43,738 (1982), which is incorporated herein by reference. Exemplary of these compounds are those represented by the formula:

R—X wherein R is a straight-chain alkyl of about 7 to 16 carbon atoms, a non-terminal alkenyl of about 7 to 22 carbon atoms, or a branched-chain alkyl of from about 13 to 22 carbon atoms, and X is —OH, —COOCH$_3$, —COOC$_2$H$_5$, —OCOCH$_3$, —SOCH$_3$, —P(CH$_3$)$_2$O, COOC$_2$H$_4$OC$_2$H$_4$OH, —COOCH(CHOH)$_4$CH$_2$OH, —COOCH$_2$CHOHCH$_3$, COOCH$_2$CH(OR")CH$_2$OR", —(OCH$_2$CH$_2$)$_m$OH, —COOR', or —CONR'$_2$ where R' is —H, —CH$_3$, —C$_2$H$_5$, —C$_3$H$_7$ or —C$_2$H$_4$OH; R" is —H, or a non-terminal alkenyl of about 7 to 22 carbon atoms; and m is 2–6; provided that when R" is an alkenyl and X is —OH or —COOH, at least one double bond is in the cis-configuration.

Solubility Enhancers

Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones and other n-substituted-alkyl-azacycloalkyl-2-ones (azones).

U.S. Pat. No. 4,537,776 to Cooper, incorporated herein by reference contains a summary of prior art and background information detailing the use of certain binary systems for permeant enhancement. European Patent Application 43,738, also describes the use of selected diols as solvents along with a broad category of cell-envelope disordering compounds for delivery of lipophilic pharmacologically-active compounds. A binary system for enhancing metaclopramide penetration is disclosed in UK Patent Application GB 2,153,223 A, consisting of a monovalent alcohol ester of a C8–32 aliphatic monocarboxylic acid (unsaturated and/or branched if C18–32) or a C6–24 aliphatic monoalcohol (unsaturated and/or branched if C14–24) and an N-cyclic compound such as 2-pyrrolidone or N-methylpyrrolidone.

Combinations of enhancers consisting of diethylene glycol monoethyl or monomethyl ether with propylene glycol monolaurate and methyl laurate are disclosed in U.S. Pat. No. 4, 973,468 for enhancing the transdermal delivery of steroids such as progestogens and estrogens. A dual enhancer consisting of glycerol monolaurate and ethanol for the transdermal delivery of drugs is described in U.S. Pat. No. 4,820,720. U.S. Pat. No. 5,006,342 lists numerous enhancers for transdermal drug administration consisting of fatty acid esters or fatty alcohol ethers of C$_2$ to C$_4$ alkanediols, where each fatty acid/alcohol portion of the ester/ether is of about 8 to 22 carbon atoms. U.S. Pat. No. 4,863,970 discloses penetration-enhancing compositions for topical application including an active permeant contained in a penetration-enhancing vehicle containing specified amounts of one or more cell-envelope disordering compounds such as oleic acid, oleyl alcohol, and glycerol esters of oleic acid; a C$_2$ or C$_3$ alkanol and an inert diluent such as water.

Other chemical enhancers, not necessarily associated with binary systems, include dimethylsulfoxide (DMSO) or aqueous solutions of DMSO such as those described in U.S. Pat. No. 3,551,554 to Herschler; U.S. Pat. No. 3,711,602 to Herschler; and U.S. Pat. No. 3,711,606 to Herschler, and the azones (n-substituted-alkyl-azacycloalkyl-2-ones) such as noted in U.S. Pat. No. 4,557,943 to Cooper.

Some chemical enhancer systems may possess negative side effects such as toxicity and skin irritations. U.S. Pat. No. 4,855,298 discloses compositions for reducing skin irritation caused by chemical enhancer-containing compositions having skin irritation properties with an amount of glycerin sufficient to provide an anti-irritating effect.

Combinations of Lipid Bilayer Disrupting Agents and Solvents

Ethanol and the unsaturated fatty acid linoleic acid were combined (LA/ethanol) and studied as described in the following examples. Single component enhancer formulations, including polyethylene glycol 200 dilaurate (PEG), isopropyl myristate (IM), glycerol trioleate (GT), ethanol/pH 7.4 phosphate buffered saline in a one-to-one ratio (50% ethanol), and PBS were also examined.

The examples compare the effects and mechanisms of (i) a series of chemical enhancers, and (ii) the combination of these enhancers and therapeutic ultrasound (1 MHz, 1.4 W/cm2) on transdermal drug transport. Initial/ comprehensive experiments were performed with a model drug, corticosterone, and a series of chemical enhancer formulations, including polyethylene glycol 200 dilaurate (PEG), isopropyl myristate (IM), glycerol trioleate (GT), ethanol/pH 7.4 phosphate buffered saline in a one-to-one ratio (50% ethanol), 50% ethanol saturated with linoleic acid (LA/ethanol), and phosphate buffered saline (PBS).

Passive experiments without ultrasound) with PEG, IM, and GT resulted in corticosterone flux enhancement values of only 2, 5, and 0.8, relative the to the passive flux from PBS alone. However, 50% ethanol and LA/ethanol significantly increased corticosterone passive fluxes by factors of 46 and 900. These passive flux enhancements were due to (1) the increased corticosterone solubility in the enhancers, and (2) interactions of linoleic acid with the skin. Specifically, linoleic acid increased the corticosterone permeability by nearly 20-fold over that from 50% ethanol alone. Therapeutic ultrasound (1 MHz, 1.4 W/cm$^2$) and the chemical enhancers utilized together produced corticosterone fluxes from PBS, PEG, IM, and GT that were greater than the passive fluxes from the same enhancers by factors of between 1.3 and 5.0, indicating that the beneficial effects of chemical enhancers and therapeutic ultrasound can be effectively combined. Ultrasound combined with 50% ethanol produced a 2-fold increase in corticosterone transport above the passive case, but increased by 14-fold the transport from LA/Ethanol. The combination of increased corticosterone solubility in and permeability enhancement from LA/ethanol and ultrasound yields a flux of 0.16 mg/cm$^2$/hr, 13,000-fold greater than that from PBS alone.

In order to assess the generality of enhancement ability of LA/ethanol and ultrasound, further experiments were performed with two additional model drugs, dexamethasone and testosterone. As with corticosterone, the solubilities in and passive permeabilities from LA/ethanol were much larger than those from PBS alone for dexamethasone and testosterone. The sonophoretic permeabilities from LA/ethanol were also greater for these two drugs than the passive permeabilities. Moreover, the permeability enhancements of the three drugs resulting from the addition of linoleic acid to 50% 3thanol exhibited a clear size dependence, with the degree of enhancement increasing with the size of the drug. The degree of permeation enhancement achieved by adding linoleic acid to 50% ethanol and applying ultrasound exhibits a similar size dependence. These results suggest that linoleic acid and therapeutic ultrasound, which are both lipid bilayer disordering agents, shift the transport of lipophilic molecules from the passive regime to a regime with a very weak size dependence.

Physical Enhancers

Although principally described herein as the combination of ultrasound with chemical enhancers, physical enhancers can also be used in combination with ultrasound, alone or in combination with chemical enhancers. Physical enhancers, as used herein, include inotophoresis, elect5roporation, magnetic fields, and mechanical pressure. Ultrasound is used to permeabilize the skin followed by the application of various force fields to provide additional driving force for transdermal transport of molecules.

Electric Fields (Iontophoresis or Electroporation)

Application of ultrasound or electric current alone has been shown to enhance transdermal drug transport and blood analyte extraction. As discussed above, ultrasound-induced cavitation occurring inside or outside the skin causes disordering of the SC lipids. Oscillations of cavitation bubbles may also result in significant water penetration into the disordered lipid regions. This may cause the formation of aqueous channels through the intercellular lipids of the SC, thus allowing permeants to transport across the disordered lipid domains. Once able to diffuse across the lipid domains, molecules may diffuse across keratinocytes and hence across the entire SC.

Application of electric current enhances transdermal transport by different mechanisms. First, application of an electric field provides an additional driving force for the transport of charged molecules across the skin and second, ionic motion due to application of electric fields may induce convective flows across the skin, referred to as electroosmosis. This mechanism is believed to play a dominant role in transdermal transport of neutral molecules during iontophoresis. Iontophoresis involves the application of an electrical current, preferably DC, or AC, at a current density of greater than zero up to about 1 mA/cm$^2$. Typically, a constant voltage is applied since resistance changes over time, usually in the range of between greater than zero and four volts. Attempts have been made to enhance the skin permeability using electric current to achieve transdermal extraction of glucose Tamada, et al., *Proceed. Intern. Symp. Control. Rel. Bioact. Mater.* 22, 129–130 (1995). Although these attempts have been successful to a certain extent, the amounts of glucose extracted by these methods are several orders of magnitude lower than those which could be detected by the currently existing biosensors. The mechanism of sonophoretic transdermal glucose extraction is believed to be similar to that of sonophoretic transdermal drug delivery. Specifically, application of low-frequency ultrasound increases the skin permeability by disordering its lipid bilayers which leads to the formation of aqueous channels through the intercellular lipids of the SC. This allows faster diffusion of glucose present in the interstitial fluids across the permeabilized skin.

As used herein, ultrasound is used in combination with application of an electric current. As shown by Example 2, the results obtained using the combination are significantly better than either alone.

Mechanical or Osmotic Pressure

The advantages of combining sonophoresis with physical enhancers is not restricted to electric current. Effects on transdermal transport may also be observed between ultrasound and pressure (mechanical or osmotic) as well as between ultrasound and magnetic fields since the physical principles underlying the possible enhancement are the same. A pressure gradient can be used to enhance convection (physical movement of liquid) across the skin permeabilized by sonophoresis. This can be particularly useful in transdermal extraction of blood analytes. Application of pressure, for example, a vacuum or mechanical pressure, to the skin pretreated by sonophoresis can result in transdermal extraction of interstitial fluid which can be analyzed to measure concentration of various blood analytes.

Magnetic Fields

Application of magnetic fields to the skin pretreated with ultrasound may also result in a higher transport of magnetically active species across the skin. For example, polymer microspheres loaded with magnetic particles could be transported across the skin using sonophoresis and magnetic fields.

The combination of sonophoresis with any of these additional physical mechanisms for enhanced transport provides the following advantages over sonophoresis or the physical enhancers alone: i) It allows lowering application times to deliver a given drug dose or extract a certain amount of analytes compared to the required times in the presence of ultrasound or one of the other enhancers alone; ii) It reduces the magnitude of the required ultrasound intensity and electric current or pressure to achieve a given transdermal flux compared to that required if, the enhancers were used alone; and iii) It can be used to provide a better control over transdermal transport of molecules compared to that obtained using an enhancer alone.

Drug Delivery

Drugs to be Administered

Drugs to be administered include a variety of bioactive agents, but are preferably proteins or peptides. Specific examples include insulin, erythropoietin, and interferon. Other materials, including nucleic acid molecules such as antisense and genes encoding therapeutic proteins, synthetic organic and inorganic molecules including antiinflammatories, antivirals, antifungals, antibiotics, local anesthetics, and saccharides, can also be administered.

The drug will typically be administered in an appropriate pharmaceutically acceptable carrier having an absorption coefficient similar to water, such as an aqueous gel. Alternatively, a transdermal patch such as the one described in the examples can be used as a carrier. Drug can be administered in a gel, ointment, lotion, suspension or patch, which can incorporate anyone of the foregoing.

Drug can also be encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof. The microparticles can have diameters of between 0.001 and 100 microns, although a diameter of less than 10 microns is preferred. The microparticles can be coated or formed of materials enhancing penetration, such as lipophilic materials or hydrophilic molecules, for example, polyalkylene oxide polymers and conjugates, such as polyethylene glycol. Liposome are also commercially available.

Administration of Drug

The drug is preferably administered to the skin at a site selected based on convenience to the patient as well as maximum drug penetration. For example, the arm, thigh, or stomach represent areas of relatively thin skin and high surface area, while the hands and feet are uneven and calloused. In the preferred embodiment, drug is applied to the site and ultrasound applied immediately thereafter. Chemical and physical enhancers can be applied before, during or immediately after the ultrasound. Chemical enhancers are preferable administered during or before ultrasound.

Based on these calculations and the data in the following examples, one can calculate the required dosage and application regime for treatment of a patient, as follows. A typical diabetic patient (70 Kg weight) takes about 12 Units of insulin three times a day (total dose of about 36 Units per day: cited in 'World Book of Diabetes in Practice' Krall, L. P. (Ed), Elsvier, 1988). If each insulin dose was to be delivered by sonophoresis in 1 hour, the required transdermal flux would be 12 U/hour. Note that 1 unit (1 U) of insulin corresponds approximately to 40 mg of insulin. The transdermal patch area used in these calculations is 40 cm$^2$ (the area of a transdermal FENTANYL™ patch [ALZA Corporation]). The donor concentrations used in these calculations are 100 U/ml in the case of insulin (commercially available insulin solution [Humulin]), $3 \times 10^7$ in the case of γ-interferon (typical concentration of interferon solution recommended by Genzyme Corporation), and $3 \times 10^5$ U/ml in the case of erythropoeitin [Davis, et al., *Biochemistry*, 2633–2638, 1987].

A typical γ-interferon dose given each time to patients suffering from cancer or viral infections is about $5 \times 10^6$ U [(i) Grups, et al., *Br. J. Med.*, 1989, 64 (3): 218–220, (ii) Parkin, et al., *Br. Med. J.*, 1987, 294: 1185–1186]. Similar doses of α-interferon and β-interferon have also been shown to enhance the immune response of patients suffering from viral infections and cancer (cited in 'Clinical Applications of interferons and their inducers', Ed. Stringfellow D., Marcel Dekker, New York, 1986). If this interferon dose was to be given by sonophoresis in 1 hour, the required transdermal flux would be $5 \times 10^6$ U/hour. Note that 1 unit of γ-interferon corresponds approximately to 1 pg of γ-interferon.

A typical daily erythropoeitin dose given subcutaneously to anemic patients is about 400 U (cited in 'Subcutaneous Erythropoeitin, Bommer J., Ritz E., Weinreich T., Bommer G., Ziegler T., Lancet, 406, 1988). If this dose was to be delivered in three steps, each involving sonophoresis for 1 hour, the transdermal flux required would be about 140 U/hour. Note that 1 unit of erythropoeitin corresponds approximately to 7.6 nanograms of erythropoeitin.

Optimal selection of ultrasound parameters, such as frequency, pulse length, intensity, as well as of non-ultrasonic parameters, such as ultrasound coupling medium, can be conducted to ensure a safe and efficacious application using the guidelines disclosed herein as applied by one of ordinary skill in the art.

Measurement of Analytes Analytes to be Measured

A variety of analytes are routinely measured in the blood, lymph or other body fluids. Measurements usually require making a puncture in order to withdraw sample. Examples of typical analytes that can be measured include blood sugar (glucose), cholesterol, bilirubin, creatine, various metabolic enzymes, hemoglobin, heparin, vitamin K or other clotting factors, uric acid, carcinoembryonic antigen or other tumor antigens, and various reproductive hormones such as those associated with ovulation or pregnancy. Transdermal drug delivery, in combination with the non-invasive blood analyte measurements, may be used to formulate self-regulated drug delivery methods which provide: a close control of the blood concentrations, minimal pain, and better patient compliance. Non-invasive blood analysis method includes extraction of various analytes from the skin's interstitial fluids (where the analytes are present at a concentration proportional to the blood concentration) across the skin into a patch, solution or gel, where their concentration can be measured using biosensors. This method of blood analyte measurements should be particularly useful in the case of diabetic patients who require multiple daily blood glucose measurements.

Measurement of Analytes

The ultrasound is applied to the skin at the site where the sample is to be collected. A reservoir or collecting container is applied to the site for collection of the sample, which is then measured using standard techniques. The ultrasound conditions are optimized as in the case for drug delivery, to maximize analyte recovery, while maintaining the relative levels of the analyte to other components of the sample. Chemical and/or physical enhancers are applied to the site before, during and after the ultrasound, preferably during or before the ultrasound.

The present invention will be further understood by reference to the following non-limiting examples.

EXAMPLE 1

Effect of Ultrasound Intensity and Chemical Enhancers on Transdermal Transport

Materials

Human cadaver skin from the chest, back, and abdominal regions was obtained from local hospitals and the National Disease Research Institute. The skin was stored at −80° C. until usage. The epidermis was separated from the full-thickness tissue after immersion in 60° C. water for 2 minutes. Heat-stripped skin was stored at 5° C. and 95% humidity for up to 1 week prior to usage. $^3$H-corticosterone, $^3$H-dexamethasone, $^3$H-testosterone, and $^{14}$C-linoleic acid were obtained from DuPont, New England Nuclear. Non-radiolabeled corticosterone (95%), dexamethasone (99+%), testosterone (99+%), and linoleic acid (99%) were obtained from Sigma Chemical. Glycerol trioleate (99+%) and Polyethylene glycol 200 Dilaurate (99+%) were obtained from Henkel. Isopropyl myristate (98%) was obtained from Aldrich Chemicals and butanediol (98%) was obtained from ISP Technologies. Ethanol was obtained from Pharmco Products.

A. Methods for Passive permeability experiments

The passive permeabilities (e.g., permeability without the application of ultrasound) of corticosterone, dexamethasone, and testosterone through human skin were measured using trace quantities of radiolabelled drug. The radiolabelled drugs were rotary evaporated in order to remove the ethanol in which they were shipped and any tritium which had reverse exchanged onto it. The radiolabelled drugs were then redissolved in an enhancer formulation to a typical concentration of 1 μCi/ml, and added to the donor chamber of the permeation cell. Passive permeation experiments were performed using stirred side-by-side diffusion cells (Crown Glass, #DC-100B). The receiver compartment always contained pH 7.4 phosphate buffer saline (PBS, phosphate concentration =0.01 M, NaCl concentration=0.137 M) (Sigma Chemical Co.). The concentrations of radiolabelled drug in the donor and receiver compartments were measured using a scintillation counter (model 2000 CA, Packard Instruments). A minimum of three experiments were performed with each enhancer formulation.

The permeability values were calculated under steady-state conditions from the relationship $P=(dN_r/dt)/(AC_d)$ where A is the surface area of the skin sample, $C_d$ is the drug concentration in the donor chamber, and $N_r$ is the cumulative amount of drug which has permeated into the receptor chamber. The experimentally observed lag-times for the permeation experiments were 1 to 6 hours for corticosterone, 2 to 8 hours for dexamethasone, and less than 1 hour for testosterone. The variability of the individual permeability values were consistent with previously established inter-subject variability of the human skin permeability of 40%, as reported by Williams, et al., Int. J. Pharm. 86, 69–77 (1992). The passive permeability enhancements, $E_p$, were calculated relative to the passive permeability from PBS according to Eq. (1):

$$\epsilon_p \equiv \frac{P(\text{enhancer})}{P(PBS)} \quad (1)$$

where P(enhancer) is the drug permeability from a given enhancer, and P(PBS) is the drug permeability from PBS. The fluxes from saturated solutions, $J^{sat}$, were calculated from $J^{sat}=PC^{sat}$, where $C^{sat}$ is the drug solubility in the formulation. Flux enhancements, $E_j$, were calculated using Eq. (2), $$\epsilon_J \equiv \frac{J(\text{enhancer})}{J(PBS)} \quad (2)$$

where $J^{sat}$ (enhancer) and $J^{sat}$(PBS) are the drug fluxes from saturated solutions of enhancer and PBS, respectively.

The results of the passive corticosterone transport experiments are shown in Table 1.

TABLE 1

Corticosterone Transport Properties With Chemical Enhancers

| Enhancer | Steady-State Permeability, P (cm/hr × 10$^5$) | Permeability Enhancement, $\epsilon_p$ | Solubility, C$^{sat}$ (mg/ml) | Saturated Flux, J$^{sat}$ (mg/cm$^2$/hr × 10$^5$) | Flux Enhancement, $\epsilon_j$ |
|---|---|---|---|---|---|
| Phosphate buffer | 10 ± 32% | 1.0 | 0.12 | 1.2 | 1.0 |
| PEG 200 Dilaurate | 2.4 ± 29% | 0.24 | 0.94 | 2.2 | 1.9 |

TABLE 1-continued

Corticosterone Transport Properties With Chemical Enhancers

| Enhancer | Steady-State Permeability, P (cm/hr × $10^5$) | Permeability Enhancement, $\epsilon_p$ | Solubility, $C^{sat}$ (mg/ml) | Saturated Flux, $J^{sat}$ (mg/cm$^2$/hr × $10^5$) | Flux Enhancement, $\epsilon_j$ |
|---|---|---|---|---|---|
| Isopropyl Myristate | 7.0 ± 38% | 0.70 | 0.77 | 5.4 | 4.5 |
| Glycerol trioleate | 7.1 ± 29% | 0.71 | 0.14 | 1.0 | 0.8 |
| 50% Ethanol 50% Buffer | 5.2 ± 21% | 0.52 | 9.2 | 48 | 40 |
| Linoleic acid in 1:1 Ethanol:Buffer | 87 ± 34% | 8.7 | 12.4 | 1080 | 903 |

The results reveal that the enhancer formulations fall into two groups. The first group of chemical enhancers, PEG, IM, and GT, produced only modest effects upon corticosterone transport, while the second group, 50% Ethanol and LA/Ethanol, had a significant impact. With respect to the first group, PEG and IM are better solubilizers of corticosterone, with measured solubilities of 0.94 and 0.77 mg/ml. The solubility of corticosterone in PBS is considerably lower, 0.12 mg/ml, but is similar to the solubility of corticosterone in GT, 0.14 mg/ml, as shown in Table 1. These increases in solubility for PEG and IM, however, do not translate into significantly greater saturated fluxes than that from PBS. This is due to the decreases in the corticosterone permeabilities from PEG and IM relative to that from PBS. Specifically, the measured corticosterone permeability from PBS is $1.0 \times 10^{-4}$ cm/hr, while those from PEG and IM are only $2.4 \times 10^{-5}$ and $7.0 \times 10^{-14\ 5}$ cm/hr, as shown in Table 1. As a result, the flux enhancements from PEG and IM are moderate, 1.9 and 4.5, respectively. GT, whose corticosterone solubility is similar to that of PBS, also has a corticosterone permeability, $7.1 \times 10^{-5}$ cm/hr, which is similar to that of PBS, $1.0 \times 10^{-4}$ cm/hr, as shown in Table 1. Thus, the corticosterone flux from a saturated solution of GT, $1.0 \times 10^{-5}$ mg/cm$^2$/hr, is similar to that from saturated PBS, $1.2 \times 10^{-5}$ mg/cm$^2$/hr. In summary, the differences in the solubilities, permeabilities, and fluxes of corticosterone from PBS, PEG, IM, and GT are all relatively moderate.

In contrast, 50% Ethanol and LA/Ethanol significantly increase the transdermal transport of corticosterone. The permeability of corticosterone from 50% Ethanol, $5.2 \times 10^{-5}$ cm/hr, is nearly two-fold lower than that from PBS, $1.0 \times 10^{-4}$ cm/hr, and in the same range as those from PEG, IM, and GT as well. However, 50% Ethanol is a very effective solubilizer. 9.2 mg/ml is the corticosterone solubility in 50% Ethanol, which is nearly 100-fold greater than that in PBS, 0.12 mg/ml, as shown in Table 1. This greater degree of solubilization results in a significantly greater flux of $4.8 \times 10^{-4}$ mg/cm$^2$/hr, which is a factor of 40 greater than of that from PBS.

Even more effective is LA/Ethanol, which is 50% ethanol (v/v) saturated with linoleic acid. Table 1 shows that the corticosterone permeability from LA/Ethanol is $8.7 \times 10^{-4}$ cm/hr. Note that all of the other formulations have lower permeabilities than from PBS, while the permeability from LA/Ethanol is nine-fold greater. The permeability enhancement achieved through the mere addition of linoleic acid to 50% Ethanol is 17-fold, clearly showing the effectiveness of the unsaturated fatty acid in increasing transport. Addition of linoleic acid to 50% Ethanol increases the corticosterone solubility to 12.4 mg/ml in LA/Ethanol from 9.2 mg/ml in 50% Ethanol alone, as shown in Table 1. Addition of the oily linoleic acid tends to make the solution more hydrophobic and slightly less polar, which is a more attractive environment for corticosterone. The combination of permeation enhancement and increased corticosterone solubility arising from the use of linoleic acid in 50% Ethanol combine to yield saturated drug fluxes of $1.1 \times 10^{-3}$ mg/cm$^2$/hr, which is 903-fold greater than from water and more than 20-fold greater than from 50% Ethanol (i.e., without the linoleic acid).

In order to examine the impact of linoleic acid on corticosterone transport without coupling it with 50% Ethanol, control experiments were performed in which corticosterone permeabilities were measured from PBS saturated with linoleic acid. The resulting corticosterone permeability, $1.1 \times 10^{-4}$ ($\pm 0.34 \times 10^{-4}$) cm/hr, is indistinguishable from the PBS permeability of $1.0 \times 10^{-4}$ ($\pm 0.32 \times 10^{-4}$) cm/hr reported in Table 1. Clearly, ethanol and linoleic acid are each ineffective in increasing corticosterone permeability when utilized individually, but when utilized together, they yield a substantial degree of enhancement.

B. Effect of Ultrasound in Combination with Chemical Enhancers

Ultrasound was applied under therapeutically approved conditions (1.4 W/cm$^2$, 1 MHz, continuous) for 24 hours using a sonicator (Sonopuls 463, Henley International). The ultrasound transducer was located approximately 3 cm from the surface of the skin. Permeation experiments were performed using customized side-by-side diffusion cells having a skin area of 3.1 cm$^2$ and a receiver compartment volume of 7.5 ml. Samples were taken from the receiver compartment over 24 hours. The concentrations of radiolabelled drug in these samples, as well as in the donor compartment, were measured using a scintillation counter (model 2000 CA, Packard Instruments). Three or more experiments were performed using each of the chemical enhancers listed above. PBS was always used in the receiver compartment. Sonophoretic permeabilities were constant once steady-state was achieved. The drug permeabilities in the presence of ultrasound were $P_{us} = (dN_r/d_t)/(AC_d)$. The exception to this observation was the combination of therapeutic ultrasound and SA/Ethanol, with which the corticosterone permeability continually increased.

Studies with therapeutic ultrasound 1 MHz performed at an intensity of 2.0 W/cm² by Mitragortri, et al. *J. Pharm. Sci.* 84, 697–706 (1995) showed that the continuous application of ultrasound increased transdermal permeabilities, but only for a short period of time. After 5 to 6 hours, the sonophoretic enhancement abated and the observed permeabilities returned to the passive values. This sonophoretic enhancement was found to be caused by cavitation within the skin, where cavitation is defined as the growth and oscillation of air bubbles which disorder the stratum corneum lipid bilayers. In the present study, ultrasound was applied at a lower intensity, 1.4 W/cm², and 1 MHz. Sonophoretic permeability enhancements lasted for extended periods of time for corticosterone, dexamethasone, and testosterone at this intensity. The elevated transdermal permeabilities resulting from the continuous application of ultrasound at 1.4 W/cm² were maintained for up to 48 hours, the longest sonophoretic experiment performed. As a control, the permeability of corticosterone was measured with therapeutic ultrasound applied at 2.0 W/cm². As was previously found and reported for estradiol, the permeation enhancement lasted for only 5 to 6 hours. This difference in the duration of the sonophoretic enhancements resulting from differences in the ultrasound intensity is probably due to the change in the magnitude of the cavitation activity. Since cavitation results in the degassing of the system, the greater ultrasound intensity results in an accelerated degassing of the system, which in turn results in shorter duration of the permeability enhancements, as was observed.

The transmission efficiency of ultrasound through the various enhancers was measured using a hydrophone (model PZT 54, Specialty Engineering Associates) coupled to a hydrophone preamplifier (model A17DB, Specialty Engineering Associates), and connected to an oscilloscope (model 7623 A, Hewlett Packard). The hydrophone was calibrated by Sonic Technologies. The ultrasound intensity in the diffusion cell was first measured with both probes submerged in the formulation and the hydrophone in close proximity to the ultrasound transducer. The ultrasound intensity was subsequently measured with the transducer in the donor chamber of the permeation cell and the hydrophone in the receiver chamber 5–6 cm away from the transducer. No differences in the measured intensities were observed for any formulation, indicating that all of the chemical enhancer formulations examined were uniformly efficient in transmitting ultrasound.

The uptake of $^{14}$C-linoleic acid into human SC was measured with and without the application of therapeutic ultrasound (1.4 W/cm², 1 MHz, continuous). SC was separated from heat stripped epidermis by soaking the epidermis in 0.5% Trypsin solution overnight at 5° C. The SC was cleaned with water, rinsed in cold hexane to remove any exogenous lipids, and lyophilized for at least 24 hours to remove all water. Dried pieces of SC were sectioned into pieces approximately 10 mg in weight and weighed. These SC pieces were place in a glass chamber mounted on an ultrasound probe containing 3 ml of solution of $^{14}$C-linoleic acid in LA/Ethanol and sealed. 25 μl samples were taken from the chamber periodically, and counted with the liquid scintillation counter.

Ultrasound is effective in increasing the permeability of corticosterone from all of the formulations examined, as shown in Table 2.

TABLE 2

Ultrasound-Mediated Permeability Enhancement of Corticosterone

| Enhancer | Permeability Without Ultrasound, P (cm/hr × 10⁵) | Permeability With Ultrasound, $P_{us}$ (cm/hr × 10⁵) | Ultrasound Enhancement $\epsilon_{p,us}$ |
|---|---|---|---|
| Phosphate buffer | 10 ± 32% | 50 ± 39%* | 5.0 |
| PEG 200 Dilaurate | 2.4 ± 29% | 4.5 ± 24% | 1.9 |
| Isopropyl Myristate | 7.0 ± 38% | 25 ± 34% | 3.6 |
| Glycerol trioleate | 7.1 ± 29% | 9.3 ± 36% | 1.3 |
| 50% Ethanol 50% Buffer | 5.2 ± 21% | 9.8 ± 22% | 1.9 |
| Linoleic acid in 50:50 Ethanol:Buffer | 87 ± 34% | ≧1260 ± 50% | ≧14.4 |

*Experiments were performed on skin samples which had been utilized for passive permeability measurements, such that the lag-times were already surpassed.

The values of the sonophoretic permeability enhancements, $E_{p,us}$, defined as $$\epsilon_{p,us} \equiv \frac{P_{us}}{P} \quad (3)$$

are all greater than unity. Note that $E_{p,us}$, is the ratio of the ultrasound mediated permeability in a given formulation to the passive permeability in the same formulation, and hence is a measure of the effectiveness of ultrasound with that particular formulation. Table 2 shows that ultrasound mediated permeabilities for the first group of enhancers, PBS, PEG, IM, and GT, are all moderate, ranging from 1.3 for GT to 5.0 for water. The sonophoretic enhancement from 50% Ethanol, 1.9, is also moderate in its value. The most significant sonophoretic enhancement is obtained with the formulation containing linoleic acid, LA/Ethanol. The sonophoretic permeability from LA/Ethanol is 1.3×10⁻² cm/hr , which is a factor of 14 greater than the passive corticosterone permeability from LA/Ethanol. These results clearly show that ultrasound is effective in increasing transdermal drug permeation when utilized with both aqueous as well as non-aqueous formulations.

Sonophoretic Saturated Fluxes and Enhancement

The values of the ultrasound mediated corticosterone fluxes from saturated solution, $J_{us}$, where $J_{us} = P_{us} C^{sat}$, are listed in Table 3.

TABLE 3

Enhancement of Corticosterone Transport by Chemical Enhancers and Ultrasound

| Enhancer | Sonophoretic Saturated Flux, $J_{us}$ (mg/cm²/hr × 10⁵) | Sonophoretic Saturated Flux Enhancement, $\epsilon_{j,us}$ |
|---|---|---|
| Phosphate buffer | 6.0 | 5.0 |
| PEG 200 Dilaurate | 4.2 | 3.5 |
| Isopropyl Myristate | 20 | 16 |

TABLE 3-continued

Enhancement of Corticosterone Transport
by Chemical Enhancers and Ultrasound

| Enhancer | Sonophoretic Saturated Flux, $J_{us}$ (mg/cm$^2$/hr × 10$^5$) | Sonophoretic Saturated Flux Enhancement, $\epsilon_{j,us}$ |
|---|---|---|
| Glycerol trioleate | 1.3 | 1.1 |
| 50% Ethanol 50% Buffer | 90 | 75 |
| 1% Linoleic acid in 50:50 Ethanol:Buffer | ≧15,600 | ≧13,000 |

The fluxes from PBS, PEG, IM and GT are all fairly low, ranging from $1.3 \times 10^{-5}$ mg/cm$^2$/hr for GT to $6.0 \times 10^{-5}$ mg/cm$^2$/hr for PBS. The flux from PBS is greater than those from PEG, IM, and GT, due to greater sonophoretic permeability enhancement for PBS, shown in Table 2. While the flux from 50% Ethanol is 15-fold greater than that from PBS, $9.0 \times 10^{-4}$ mg/cm$^2$/hr, it is still a relatively low value. Table 3 shows that the use of LA/Ethanol and therapeutic ultrasound yields a flux greater than or equal to 0.16 mg/cm$^2$/hr, which is more than two orders of magnitude greater than that from 50% ethanol with ultrasound. Also listed in Table 3 are the sonophoretic saturated flux enhancements, $E_{J,us}$, which is defined as $$\epsilon_{J,us} \equiv \frac{P_{us}(\text{enhancer})C^{sat}(\text{enhancer})}{P(PBS)C^{sat}(PBS)} \quad (4)$$

$E_{J,us}$ represents the flux enhancement relative to the passive flux from PBS, used to establish the base line. Moderate flux enhancements are observed for PBS, PEG, GT, and 50% Ethanol, ranging from 1.1 for GT to 75 for Ethanol. LA/Ethanol again is seen to provide tremendous flux enhancement, 13,000-fold more so than from passive PBS. This enormous enhancement is the result of the combination of ethanol, linoleic acid, and therapeutic ultrasound.

Ethanol and water (1:1, v/v) greatly increases the saturated concentration of corticosterone (Table 1). Linoleic acid increases both the corticosterone solubility in 50% Ethanol as well as the corticosterone permeability, while ultrasound further increases the drug permeability when applied in conjunction with linoleic acid.

C. Solubility measurements in chemical enhancers

In separate studies, excess unlabeled corticosterone, dexamethasone, and testosterone were each placed in several milliliters of enhancer and thoroughly mixed. After equilibration for a minimum of 24 hours the solutions were removed, centrifuged at 1000 rpm (212×g) for 10 minutes, and sampled. Samples were diluted to an appropriate concentration for high performance liquid chromatographic (HPLC) analysis utilizing the appropriate HPLC mobile phase. Methanol and water (60:40 v/v) was utilized as the mobile phase for corticosterone and testosterone, and acetonitrile and water (35:65 v/v) was utilized for dexamethasone. The mobile phases were filtered with 0.22 $\mu$m PTFE hydrophobic filters and degassed prior to usage. A $\mu$-Bondapak C18 (30 cm×4 mm, i.d.) HPLC column was used. The sample volume was 40 $\mu$l and the mobile phase flow rates were 1.4 ml/minute (corticosterone) and 2.0 ml/min. (corticosterone, dexamethasone, and testosterone). An ultraviolet detector (Waters 490) was used at a wavelength of 240 nm for all three drugs. Standards were prepared by diluting a stock solution of unlabeled drug, prepared by weight, with the mobile phases. Experiments performed in triplicate had a standard deviation of 1%.

In order to probe the generality of the effectiveness of LA/Ethanol alone and the combination of ultrasound and LA/Ethanol in enhancing corticosterone transport, experiments were performed with two additional model drugs, dexamethasone and testosterone. Passive permeability and solubility measurements were made with PBS, 50% Ethanol, and LA/Ethanol, as described above. Ultrasound mediated transport was also measured with LA/Ethanol and ultrasound with both dexamethasone and testosterone, as this was the most effective enhancement combination observed in the corticosterone experiments. The results of these experiments are shown in Table 4.

TABLE 4

Passive and Ultrasound-Mediated Transport of Dexamethasone and Testosterone

| Drug | Enhancer | Passive Permeability P (cm/hr × 10$^5$) | Solubility $C^{sat}$ (mg/ml) | Saturated Flux, $J^{sat}$ (mg/cm$^2$/hr × 10$^5$) | Sonophoretic Permeability $P_{us}$ (cm/hr × 10$^5$) | Sonophoretic Saturated Flux, $J_{us}$ (mg/cm$^2$/hr × 10$^5$) |
|---|---|---|---|---|---|---|
| Dexamethasone | Phosphate buffer | 6.4 ± 40% | 0.10 | 0.66 | | |
| | 50% Ethanol 50% Buffer | 1.7 ± 23% | 2.39 | 4.0 | | |
| | Linoleic Acid in 50% Ethanol | 217 ± 42% | 4.36 | 945 | 600 ± 8% | 2610 |
| Testosterone | Phosphate buffer | 536 ± 17% | 0.023 | 12.3 | | |
| | 50% Ethanol 50% Buffer | 5.5 ± 8% | 6.37 | 35.2 | | |
| | Linoleic Acid in 50% Ethanol | 64 ± 24% | 8.2 | 525 | 449 ± 52% | 3680 |

The solubility of dexamethasone in PBS is 0.10 mg/ml, which is similar to the solubility of corticosterone in PBS, 0.12 mg/ml. This is not surprising since dexamethesone and corticosterone have a similar degree of hydrophobicity, as revealed by their similar octanol/water partition coefficients of 97 for dexamethasone and 87 for corticosterone (Hansch and Leo, "Substitutent Constants for Correlation Analysis in Chemistry and Biology" (1979)). Testosterone is more hydrophobic than corticosterone and dexamethasone, as indicated by an octanol/water partition coefficient of 2100, has a lower solubility in PBS, 0.0234 mg/ml. Dexamethasone and testosterone are much more soluble in 50% Ethanol than PBS, 2.39 mg/ml and 6.37 mg/ml, and even more soluble in LA/ethanol, 4.36 mg/ml and 8.2 mg/ml respectively. The relative increases in drug solubility for all three drugs, corticosterone, dexamethasone, and testosterone, are shown in FIG. 1. Solubilities of corticosterone, dexamethasone, and testosterone in PBS, 50% Ethanol, and LA/ethanol were measured using HPLC. The solubilities of these drugs in PBS, 0.12 mg/ml, 0.10 mg/ml, and 0.023 mg/ml respectively, are 77, 44, and 360 fold lower than the solubilities in 50% Ethanol. Corticosterone, dexamethasone, and testosterone are even more soluble in 50% Ethanol saturated with linoleic acid (LA/Ethanol) by an average factor of 1.5.

The experimentally measured permeability of dexamethasone from PBS is $6.4 \times 10^{-5}$ cm/hr, as shown in Table 4. This value is relatively low, yet the permeability from 50% Ethanol is even lower at $1.7 \times 10^{-5}$ cm/hr. The permeability of testosterone from PBS is $5.4 \times 10^{-3}$ cm/hr, but decreases by nearly two orders of magnitude to a value of $5.510^{-5}$ cm/hr when measured from 50% Ethanol. Similar drops have been observed for corticosterone, as shown in Table 1, as well as for estradiol (Liu, et al. *Pharmaceutical Research* 8, 938–944 (1991)). These permeability decreases are a result of the decreased partitioning of the drugs into the skin. Since 50% ethanol has a lesser degree of polarity than does water, it is more attractive environment relative to PBS, and shifts the equilibrium drug distributions away from the skin and towards the donor solution. Since the skin permeability is proportional to the partition coefficient, skin permeabilities will decrease as the donor solution becomes less polar than PBS and a better solubilizer of the drugs. The permeability of dexamethasone from LA/Ethanol, $2.2 \times 10^{-3}$ cm/hr, is significantly greater than that from PBS, $6.4 \times 10^{-5}$ cm/hr, as was also observed with corticosterone. However, the permeability of testosterone from LA/Ethanol, $6.4 \times 10^{-3}$ and $5.3 \times 10^{-3}$ mg/cm$^2$/hr, are within a factor of two of the corticosterone saturated flux, $1.1 \times 10^{-2}$ mg/cm$^2$/hr.

Dexamethasone and testosterone sonophoretic transport measurements were made with LA/Ethanol, which is the most effective combination that was determined through the corticosterone experiments. The results of these experiments are shown in Table 4. As with corticosterone, the sonophoretically enhanced permeabilities of dexamethasone and testosterone increased over time. However, unlike the corticosterone experiments, these observed permeabilities become steady after 12 to 15 hours, enabling true steady-state measurements to be made: $6.0 \times 10^{-3}$ cm/hr and $4.5 \times 10^{-3}$ cm/hr for dexamethasone and testosterone, respectively. As with corticosterone, tremendous sonophoretic saturated fluxes of $2.6 \times 10^{-2}$ mg/cm$^2$/hr and $3.7 \times 10^{-2}$/hr are obtained for dexamethasone and testosterone.

Figure 2:
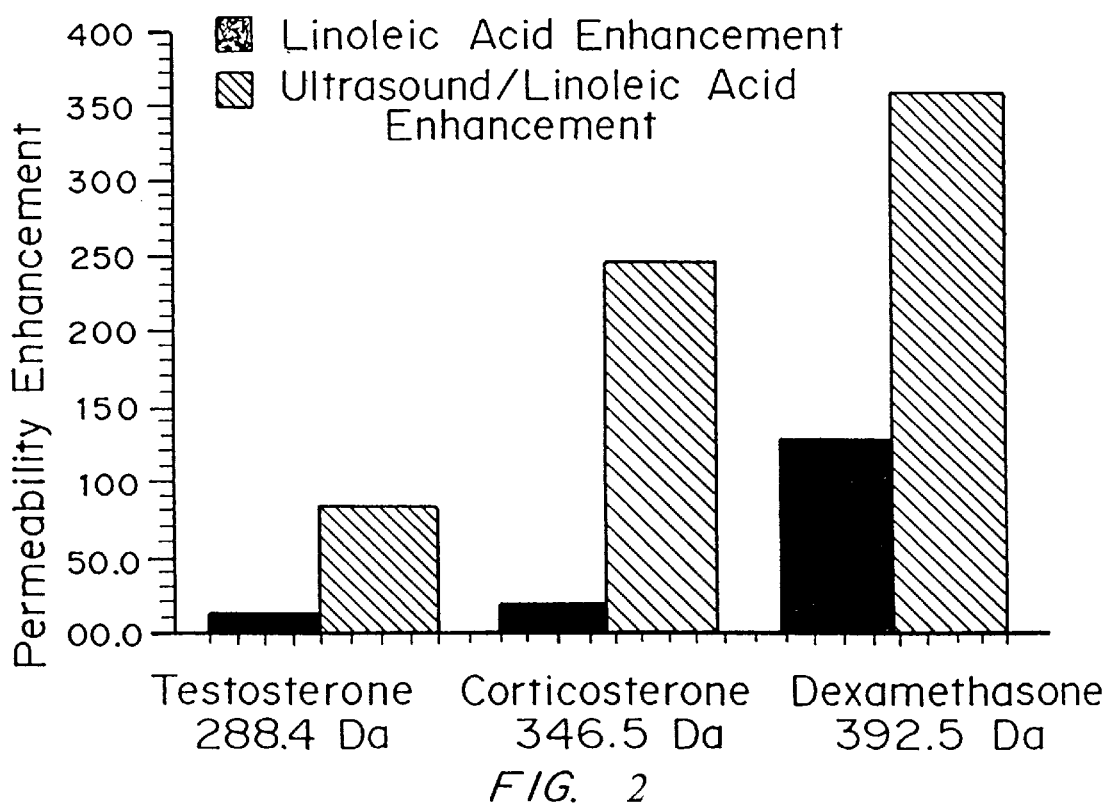
FIG. 2 is graph of the permeability enhancement for testosterone (288.4 Da), corticosterone (346.5 Da), dexamethasone (392.5 Da) in combination with linoleic acid (dark bars) and ultrasound in combination with linoleic acid enhancement (\\\\)

FIG. 2 shows that the permeation enhancement resulting from the use of linoleic acid is dependent upon the drug examined and the size of that drug. Permeability enhancements for testosterone (288.4 Da), corticosterone (346.5 Da), and dexamethasone (392.5 Da) through (1) the addition of linoleic acid to 50% ethanol and (2) the addition of linoleic acid to 50% ethanol with the continuous application of therapeutic ultrasound relative to the permeabilities from 50% ethanol alone were observed. The enhancements from linoleic acid bear a distinct size dependence, with the larger compounds having larger enhancements. Enhancements with linoleic acid and therapeutic ultrasound bears an analogous size dependence with greater enhancements observed for larger compounds. The permeation enhancements resulting from linoleic acid, (the ratio of the permeability from LA/Ethanol and the permeability from 50% ethanol) alone, are 12 for the smallest drug (testosterone, 288.4 Da), 17 for corticosterone (346.5 Da), and 130 for the largest drug (dexamethasone, 392.5 Da).

Figure 3A:
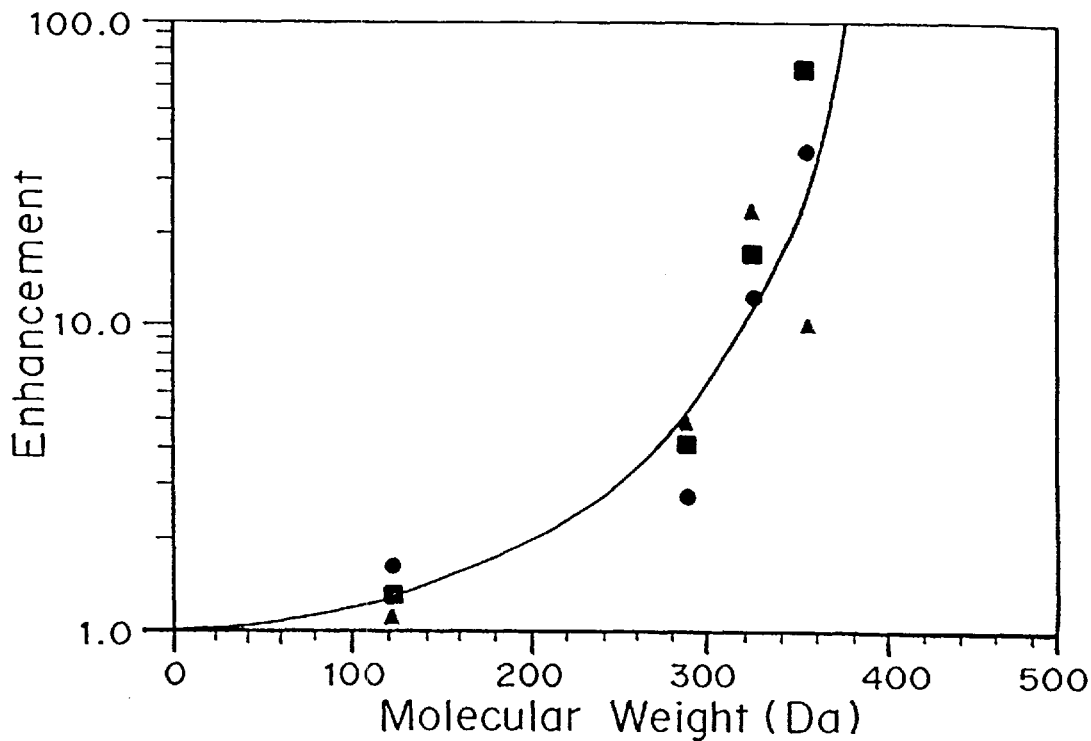
FIG. 3a is a graph of enhancement (log scale) versus molecular weight (Da).

The enhancement effects of three different enhancers, capric acid (J), lauric acid (B), and Neodecanoic acid (H), upon the human skin permeabilities of benzoic acid (122 Da), testosterone (288 Da), naloxone (328 Da), and indomethacin (359 Da), as compared with propylene glycol are shown in FIG. 3a. These enhancements exhibit a clear size dependence, with the larger compounds being enhanced to a greater degree than the smaller compounds. The line is drawn to guide the eye. The permeability values were originally reported by Aungst et al. FIG. 3a shows the permeability enhancements plotted as a function of the molecular weight of the drug. FIG. 3a also shows that the variations in enhancement of a given drug from using the different enhancers extends to be less than the variation of enhancements between the different drugs.

Figure 3B:
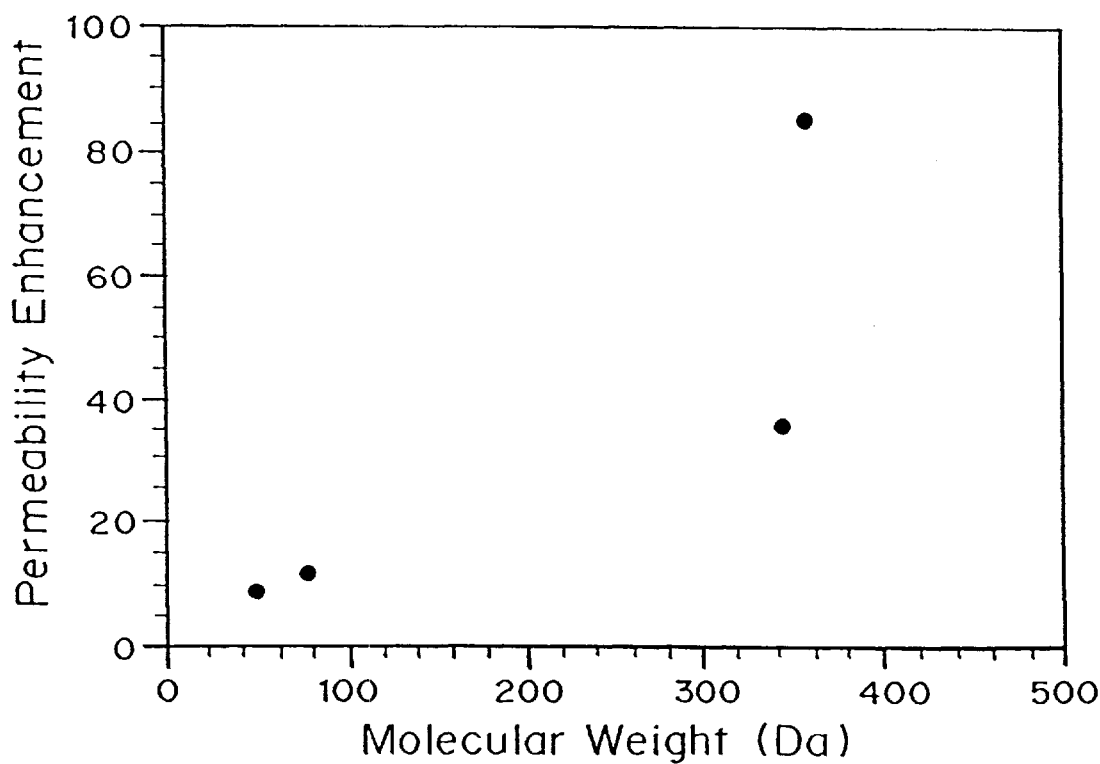
FIG. 3b is a graph of permeability enhancement versus molecular weight (Da).

The enhancement of Azone upon the permeabilities of ethanol (46 Da), butanol (74 Da), corticosterone (346 Da), and hydrocortisone (362 Da) from aqueous solutions through hairless mouse stratum corneum are shown in FIG. 3b. The skin was pretreated by spraying 0.8 mg/cm$^2$ of Azone upon it. The degree of permeability enhancement correlates with the size of the solute. The permeability values were originally reported in graphical form by Lambert et al.

Fluidization of the stratum corneum lipid bilayers can increase the partition coefficient between the bilayers and the donor medium in addition to increasing diffusion. Since partitioning is a function of the chemical nature of a solute (i.e., the hydrophobic/hydrophilic nature of a solute) and not an independent function of molecular weight, the partitioning effect would only tend to obscure the size dependence of enhancement. Linoleic acid and the other chemical enhancers may increase drug transport through alternate pathways, often referred to as aqueous pores. The passive skin permeabilities of hydrophilic compounds, which are thought to diffuse through these aqueous pores, exhibit a much weaker size dependence than that of hydrophobic compounds. While this size dependence is moderate, as are those for fluid phase phospholipid bilayers and bulk oil phases, fatty acids have been shown to interact predominantly with the intercellular lipids. Ethanol alone can also enhance transport of both hydrophobic and hydrophilic compounds through these aqueous pore pathways, although high concentrations of ethanol are needed (i.e. approximately 75% v/v). Ghanem et al., *Int. J. Pharm.* 78, 137–156 (1992) also report that lipoidal compounds in solutions of 50% ethanol or less permeate the SC primarily through the lipoidal domain. This indicates that the combination of 50% ethanol and linoleic acid may make the aqueous pore pathway more effective. If the linoleic acid worked with the 50% ethanol solution to facilitate aqueous pore transport, the passive permeabilities from LA/Ethanol would be expected to be essentially constant and independent of size. Tables 1 and 4 show that this is not the case.

The results of sonophoretic enhancement experiments conducted over the last four decades for more than a dozen different drugs, ranging in size from 138 Da (salicylic acid) up to 453 Da (fluocinolone acetonide) were collated. These studies include both in vitro and in vivo experiments. While some studies quantified the degree of enhancement, others simply reported whether or not sonophoretic enhancement was observed. All of these data are summarized in FIG. 3c, where size of the various drugs are plotted. Drugs indicated by empty circles correspond to those for which no enhancement of transdermal delivery has been observed during sonophoresis. Drugs indicated by filled circles correspond to those for which an experimentally observed enhancement has been reported. A molecular weight cut-off is observed at approximately 250 Da. No sonophoretic enhancement has been observed for drugs smaller than 250 Da whereas sonophoretic enhancement has been observed for compounds larger than 250 Da, with the lone exception of progesterone. Sonophoretic enhancement correlates very well with the drug passive diffusion coefficient, which in turn is a strong function of molecular weight.

FIG. 4 graphs the variation of the permeability over time of the corticosterone permeability through human skin from (a) PBS and (b) LA/Ethanol in the presence of therapeutic ultrasound (1 MHz, 1.4 W/cm$^2$). The corticosterone permeability from PBS is maintained at the steady-state value of the duration of the 24 experiment once the lag-time period is surpassed. The corticosterone permeability from LA/Ethanol, on the other hand, continues to increase over time. The typical error of the data points is 3%. The lines are drawn to guide the eye.

Figure 4A:
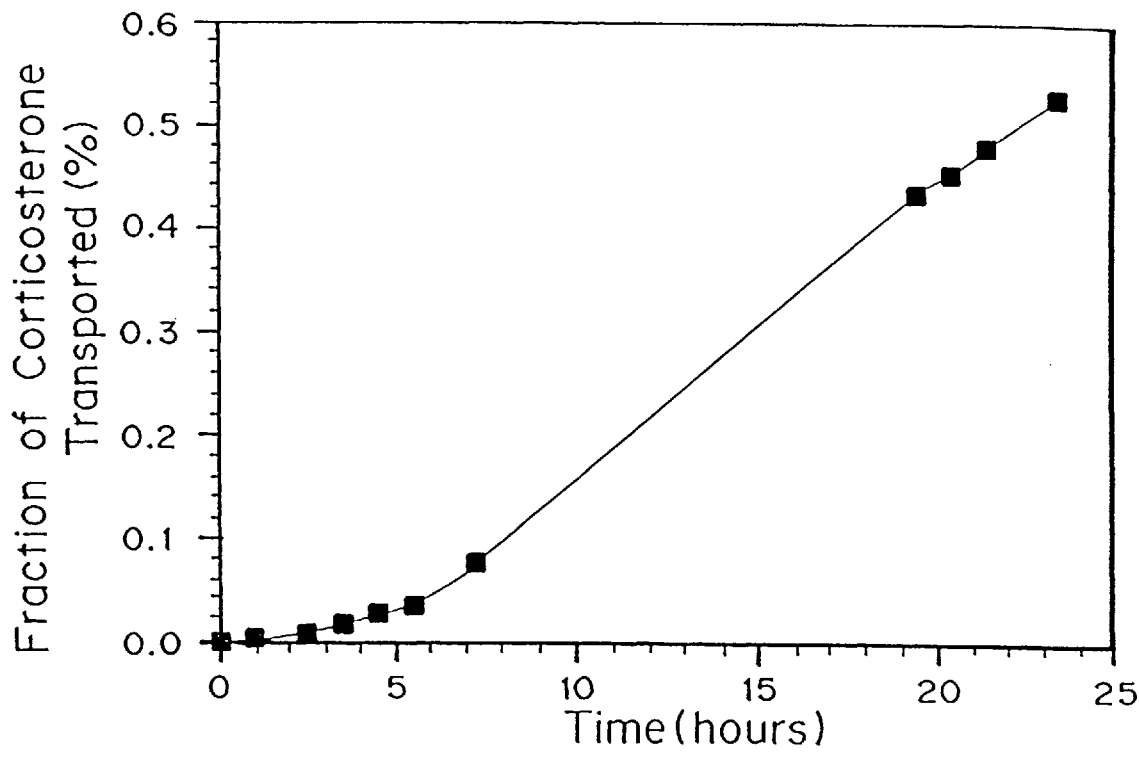
FIG. 4a is a graph of fraction of corticosterone transported (%) versus time (hours).
Figure 4B:
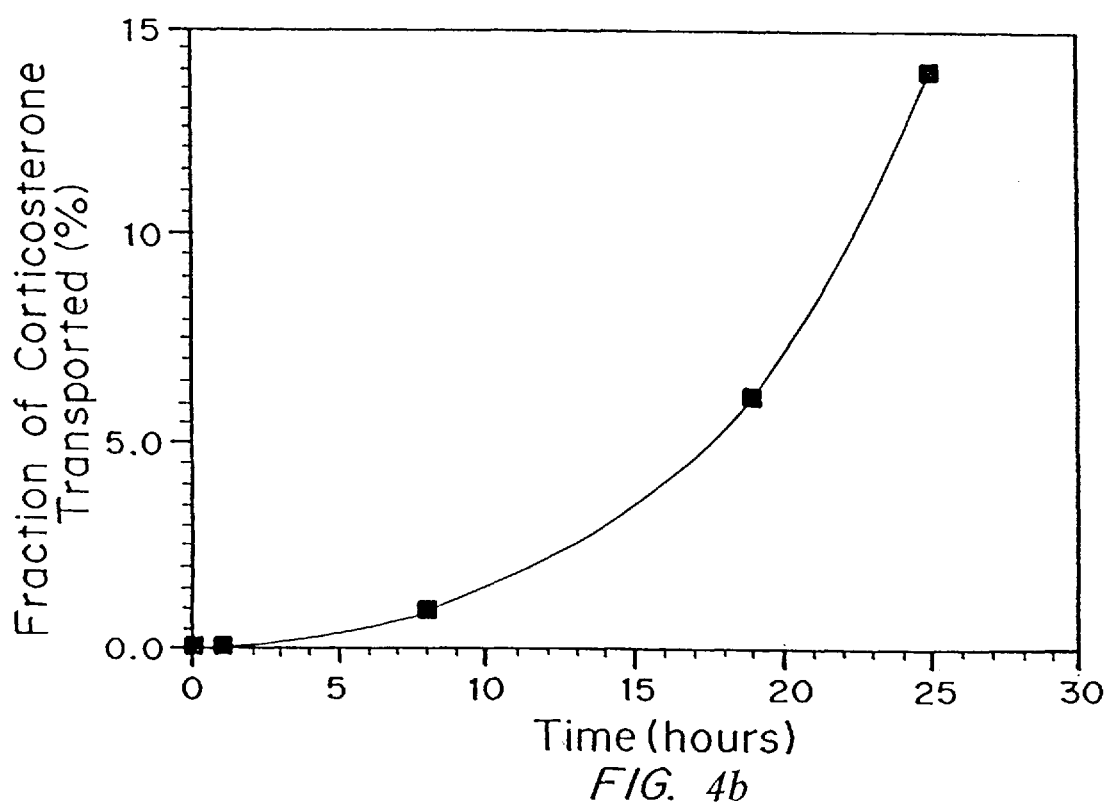
FIG. 4b is a graph of the fraction of corticosterone transported (%) versus time (hours).

The sonophoretically enhanced permeabilities were constant over time with PBS, PEG, IM, GT, and 50% Ethanol, as shown in FIG. 4a for a typical corticosterone experiment from PBS. After an initial lag time of several hours, the permeability remains constant for the duration of the 24 hour experiment. However, when ultrasound was applied in conjunction with LA/Ethanol, the corticosterone permeability continually increased. FIG. 4b shows the results of one such experiment, wherein the fraction of corticosterone transported across the skin is plotted versus time. Whereas steady-state conditions are defined by linear slope on such a plot, the slope in FIG. 4b continually increases. This continual increase in corticosterone permeability was observed in every ultrasound mediated experiment performed with corticosterone and the LA/Ethanol formulation (n=6).

A steady-state permeability can not be directly measured in the ultrasound mediated permeation experiments with LA/Ethanol due to the lack of a linear profile in FIG. 4b. The permeability value listed in Table 2 for this condition is the average of the permeabilities observed at the 24 hour mark of the experiment. While this value is not a steady-state permeability, it does constitute a lower bound on the true steady-state permeability. This value, $1.3\times10^{-2}$ cm/hr, is large relative to the other corticosterone permeabilities, and is 126-fold greater than the passive permeability from PBS alone. The true steady-state permeability is greater than or equal to $1.3\times10^{-2}$ cm/hr and the sonophoretic enhancement is greater than or equal to 14. The slightly elevated error associated with this value, a standard deviation of 50%, is also a result of the fact that the permeabilities were calculated from non-linear portions of the flux profiles, as shown in FIG. 4b.

Figure 5:
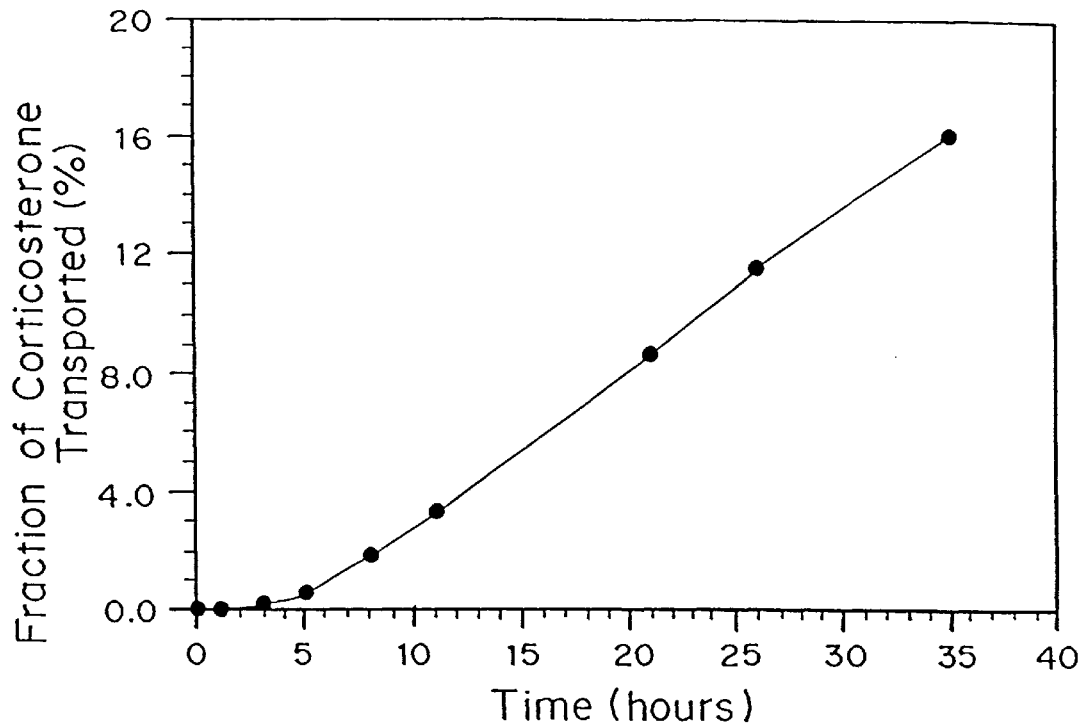
FIG. 5 is a graph of the fraction of corticosterone transported (%) versus time (hours).

The ultrasound mediated experiments performed with 50% ethanol (without linoleic acid) exhibited a constant permeability after the initial lag time. The results shown in FIG. 4b are dependent upon the combined application of linoleic acid and therapeutic ultrasound. This relationship was further probed in a set of experiments with corticosterone in LA/ethanol in which ultrasound was applied for the first eight hours of the experiments, after which the ultrasound was turned-off. The results of one such experiment are shown in FIG. 5. Variation of the permeability over time of the corticosterone permeability through human skin from LA/Ethanol with the discontinuous application of therapeutic ultrasound (1 MHz, 1.4 W/cm$^2$) is shown in FIG. 5. Ultrasound was applied for the first eight hours of the experiment, at which time it was turned off. In contrast with the results of FIG. 1b in which ultrasound was applied continuously and the permeability continued to rise for the entire 24 hour period, the corticosterone permeability increases up to the point at which the ultrasound is discontinued, at which point it remains constant for the remainder of the experiment. The typical error of the data points is 3%. The line is drawn to guide the eye.

Four possible mechanisms were considered to explain these observations:

1. Ultrasound increases drug permeabilities from PBS alone by disordering the bilayers through cavitation. However, removal of ultrasound from the PBS experiments resulted in the recovery of the permeability back to passive levels after 1–2 hours. One would also expect to see the permeability recover with LA/Ethanol if the cavitation induced bilayer disorder were solely responsible for the sonophoretically elevated permeabilities with LA/Ethanol. FIG. 5 shows that the corticosterone permeability does not decrease after the ultrasound is removed. Rather, the corticosterone permeability is maintained at the same elevated value, $7.5\times10^{-3}$ cm/hr ($\pm51\%$), nearly an order of magnitude greater than the passive permeability of $8.7\times10^{-4}$ cm/hr, for more than 24 hours after ultrasound is removed. While cavitation induced bilayer disorder is likely to be occurring, additional mechanism(s) appear to be important and necessary to explain the results presented in FIGS. 4 and 5.

2. Ultrasound might also be driving linoleic acid into the skin over time. This would increase the linoleic acid levels in the SC, which would likely result in increased bilayer fluidity relative to the passive case. To test this mechanism, the SC uptake of $^{14}$C-linoleic acid from LA/Ethanol was measured both with and without the application of therapeutic ultrasound. The rates of uptake were nearly identical over 24 hours, indicating that linoleic acid is not being driven into the skin at a significantly greater rate by ultrasound than in the passive case.

3. LA/Ethanol and ultrasound together might be inducing the extraction of the SC lipids. While this may be occurring to a minor extent, lipid extraction does not appear to be the primary mechanism. The degree of lipid removal would be essentially constant for all three drugs, since the drugs were present in trace quantities and exert no influence on the extraction process. Since SC permeabilities are inversely proportional to the lipid content, one would expect to see the same degree of increase in the sonophoretic permeability over the passive values from LA/Ethanol for the drugs examined. For example, the 14-fold increase in corticosterone permeability owing to the application of ultrasound to the passive permeability would indicate that 13/14, or 93% of the SC lipids would have to be removed.

However, the permeability increases from the application of ultrasound to LA/Ethanol for dexamethasone and testosterone are 2.8 and 7.0, which correspond to the extraction of 64% and 86% of the lipids, respectively. In addition, the donor solution contains primarily an ethanol:water solution (1:1, v/v), which is a very poor solvent system for SC lipids. In summary, the donor solution is not capable of solubilizing such large fraction of SC lipids.

4. Ultrasound may be aiding the dispersion of linoleic acid and SC lipids. Previous studies have shown that fatty acids, such as oleic acid, form segregated phases within the SC Ongpipattanakul, et al., *Pharm. Res.* 8, 350–354 (1991); Walker and Hadgraft, *Int. J. Pharm.* 71, R1–R4 (1991). Under passive conditions, linoleic acid may also tend to diffuse into the SC and collect in pools. The cavitation produced by ultrasound may induce mixing and disperse the linoleic acid and SC lipids, such that a much larger fraction of the intercellular lipoidal region contains the fluidizing agent, linoleic acid. The decreased entropy of the mixed system makes it a more favorable molecular arrangement which would remain stable even after ultrasound is stopped.

EXAMPLE 2

Transdermal Drug Delivery and Extraction of Gluose Using Ultrasound In Combination With Additional Force Fields Materials and Methods In vitro experiments were performed to study the effect of ultrasound in combination with electric currents on the delivery of calcein and extraction of glucose across human cadaver skin. The skin was heat stripped by keeping it in water at 60° C. for two minutes, followed by the removal of the epidermis. The skin was then stored at 4° C. in a humidified chamber. A piece of epidermis was taken out from the chamber prior to the experiments, and was mounted on a Franz diffusion cell (Crown Bioscientific Co.) which consists of a donor and a receiver compartment. The skin was supported by a nylon mesh (Tetko Inc.) to minimize mechanical oscillations during ultrasound application. The donor and receiver compartments were then clamped together. Two Ag/AgCl electrodes were introduced in the donor and the receiver compartment for the application of electric fields. The receiver compartment was filled with a solution of radiolabeled glucose in phosphate buffer saline (Sigma Chemicals), and the donor solution was filled with a calcein solution (Sigma Chemicals).

The ultrasound transducer was located at a distance of about 1 cm from the skin. The ultrasound was turned ON at a frequency of 20 KHz and intensity of 125 mW/cm$^2$ for 10 minutes. Electric current (0.1 mA/cm$^2$) was applied across the skin in a few experiments for 70 minutes with anode (electrode carrying the positive charge) inserted in the receiver compartment and the cathode (electrode carrying the negative charge) in the donor compartment. The concentration of calcein in the donor and the receiver compartment was measured using the spectrofluorimeter (Photon Technology Int). The concentration of glucose in the donor and the receiver compartment was measured using scintillation counter.

Figure 6:
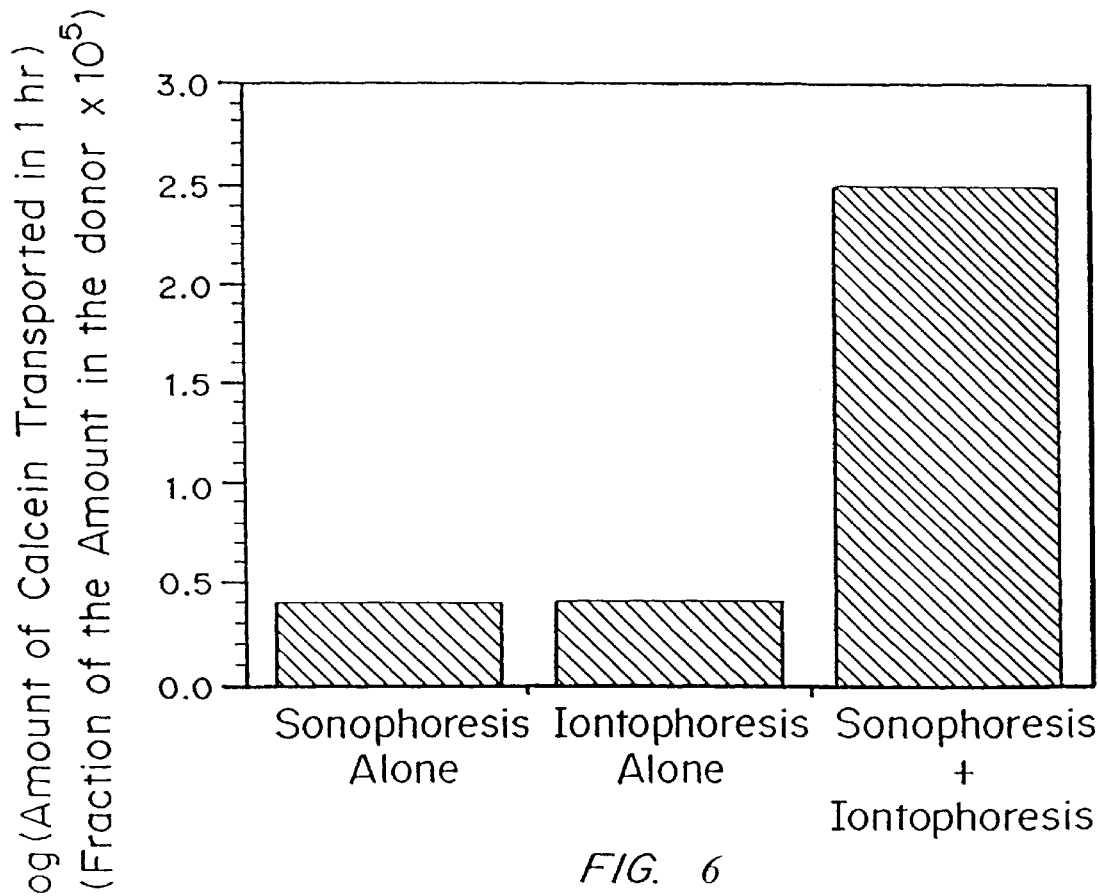
FIG. 6 is a graph of the amount of calcein transported in one hour (fraction of the amount in the donor$\times 10^5$) for sonophoresis alone, iontophoresis alone, and sonophoresis in combination with iontophoresis.

Results:

a) Transdermal Calcein Transport:

Calcein possesses a molecular weight of 622 and a net charge of −4. Due to its charge and relatively large size, passive transdermal transport of calcein is extremely low. FIG. 6 shows the transdermal transport of calcein during sonophoresis, iontophoresis or combination thereof. Sonophoresis alone at 20 KHz and 125 mW/cm$^2$ for 10 minutes followed by a waiting period of 1 hour (total time of 70 minutes) resulted in transdermal transport of about $3.2 \times 10^{-3}$% of calcein present in the donor compartment. Similarly, application of electric current (0.2 mA/cm$^2$) alone for 70 minutes induced transdermal transport $2.5 \times 10^{-6}$% of calcein present in the donor compartment. A combination of the two methods: 10 minutes of sonophoresis (20 KHz, 125 mW/cm$^2$) and 70 minutes of simultaneous iontophoresis (0.2 mA/cm$^2$) (ultrasound and electric current ON for the first 10 minutes with only iontophoresis ON for the next 60 minutes) resulted in transdermal transport of about $3.5 \times 10^{-1}$% of calcein present in the donor compartment. The results show that ransdermal calcein transport during a combined treatment of sonophoresis and iontophoresis is about 100-fold higher than that during sonophoresis or iontophoresis under similar conditions.

b) Transdermal Glucose Extraction:

Glucose is a hydrophilic molecule and shows no detectable transdermal transport passive diffusion.

Figure 7:
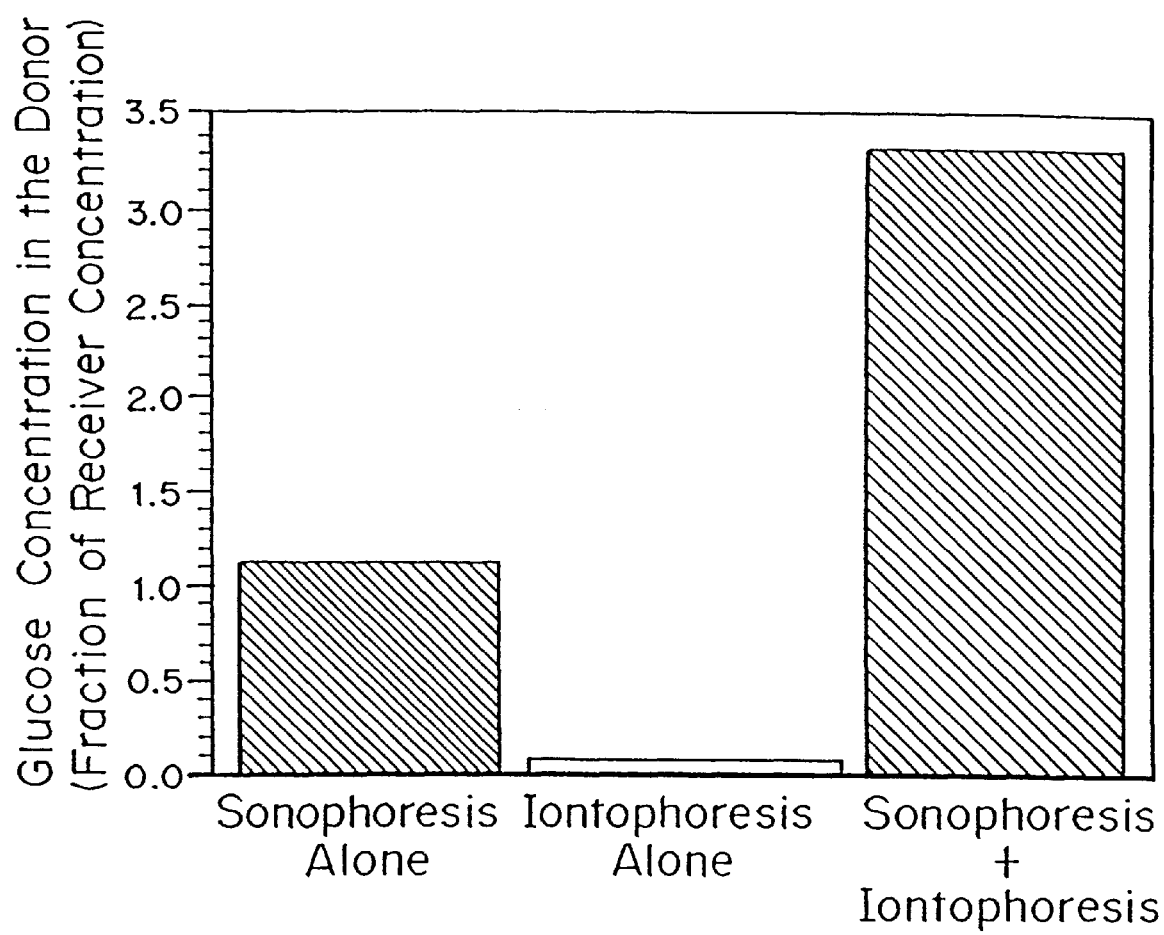
FIG. 7 is a graph of the glucose concentration in the donor (fraction of receiver concentration).

FIG. 7 shows the amount of glucose extracted transdermally by sonophoresis, iontophoresis or combination thereof. Application of ultrasound (20 KHz, 125 mW/cm$^2$) alone for 10 minutes followed by a waiting period of 1 hour (total time of 70 minutes) resulted in the donor glucose concentration of about 1% of the receiver glucose concentration. Application of electric current (0.2 mA/cm$^2$) (ultrasound and electric current ON for the first 10 minutes with only iontophoresis ON for the next 60 minutes) resulted in a donor glucose concentration which was about 3.4% of the receiver concentration. Simultaneous application of sonophoresis and iontophoresis induced about three-fold higher transdermal glucose transport than that induced by sonophoresis alone.

Modifications and variations of the present invention will be obvious to those skilled in the art from the foregoing detailed description, and are intended to come within the scope of the appended claims.

We claim:

1. A method for enhancing transdermal transport of compounds comprising administering to the skin an effective amount of ultrasound in combination with linoleic acid in an ethanol solution.

2. A method for enhancing transdermal transport of compounds comprising administering to the skin an effective amount of ultrasound in combination with a magnetic force field to transport the compound through the skin.

3. The method claim 2 comprising administering to the skin an effective amount of ultrasound and magnetic force in combination with an agent enhancing solubility of the compounds to be transported and an agent enhancing the fluidity of lipid bilayers.

4. The method of claim 1 wherein the combination is linoleic acid in an ethanol solution.

5. The method of claim 2 wherein the ultrasound is administered at a frequency of between 20 kHz and 40 kHz.

6. The method of claim 2 wherein the ultrasound is administered at a frequency of 1 MHz or less.

7. The method of claim 2 wherein the intensity of the ultrasound is less than 2.5 W/cm$^2$.

8. The method of claim 2 wherein the intensity of the ultrasound is less than 1.5 W/cm$^2$.

9. The method of claim 2 wherein the ultrasound is administered in combination with an electric force field selected from the group consisting of electroporation and iontophoresis.

10. The method of claim 2 wherein the ultrasound is administered in combination with a mechanical or osmotic force field.

11. The method of claim 2 wherein the ultrasound is administered in combination with iontophoresis.

12. The method of claim 2 wherein the compound to be transported is a drug the patient is in need of.

13. The method of claim 2 wherein the compound to be transported is an analyte to be measured.

* * * * *